(12) United States Patent
Woodyer et al.

(10) Patent No.: US 11,859,224 B2
(45) Date of Patent: *Jan. 2, 2024

(54) METHODS FOR MANUFACTURING A PRODUCT USING A 3-EPIMERASE

(71) Applicant: Tate & Lyle Solutions USA LLC, Hoffman Estates, IL (US)

(72) Inventors: Ryan David Woodyer, Hoffman Estates, IL (US); Richard W. Armentrout, Hoffman Estates, IL (US)

(73) Assignee: Tate & Lyle Solutions USA LLC, Hoffman Estates, IL (US)

( * ) Notice: Subject to any disclaimer, the term of this patent is extended or adjusted under 35 U.S.C. 154(b) by 342 days.

This patent is subject to a terminal disclaimer.

(21) Appl. No.: 17/139,605

(22) Filed: Dec. 31, 2020

(65) Prior Publication Data

US 2021/0198648 A1 Jul. 1, 2021

Related U.S. Application Data

(63) Continuation of application No. 16/370,163, filed on Mar. 29, 2019, now abandoned, which is a continuation of application No. 15/639,214, filed on Jun. 30, 2017, now Pat. No. 10,294,469, which is a continuation of application No. 14/431,549, filed as application No. PCT/GB2013/052531 on Sep. 27, 2013, now Pat. No. 9,725,707.

(60) Provisional application No. 61/706,338, filed on Sep. 27, 2012.

(30) Foreign Application Priority Data

Nov. 15, 2012 (GB) ..................... 1220554

(51) Int. Cl.
C12P 19/02 (2006.01)
C12P 19/24 (2006.01)
C12N 9/90 (2006.01)

(52) U.S. Cl.
CPC ................ C12N 9/90 (2013.01); C12P 19/02 (2013.01); C12P 19/24 (2013.01); C12Y 501/03 (2013.01)

(58) Field of Classification Search
CPC ......... C12N 9/90; C12Y 501/03; C12P 19/02; C12P 19/24
See application file for complete search history.

(56) References Cited

U.S. PATENT DOCUMENTS

| | | | |
|---|---|---|---|
| 5,411,880 A | 5/1995 | Izumori et al. | |
| 5,679,562 A | 10/1997 | Izumori et al. | |
| 8,008,058 B2 | 8/2011 | Maruta et al. | |
| 8,030,035 B2 | 10/2011 | Oh et al. | |
| 8,216,818 B2 | 7/2012 | Maruta et al. | |
| 8,735,106 B2 | 5/2014 | Hong et al. | |
| 9,259,022 B2 | 2/2016 | Woodyer et al. | |
| 9,491,960 B2 | 11/2016 | Woodyer et al. | |
| 9,635,879 B2 | 5/2017 | Woodyer et al. | |
| 9,725,707 B2 | 8/2017 | Woodyer et al. | |
| 9,854,827 B2 | 1/2018 | Woodyer et al. | |
| 10,294,469 B2 | 5/2019 | Woodyer et al. | |
| 2007/0116821 A1 | 5/2007 | Prakash et al. | |
| 2009/0304891 A1 | 12/2009 | Fujihara et al. | |
| 2010/0129865 A1 | 5/2010 | Maruta et al. | |
| 2010/0190225 A1 | 7/2010 | Oh et al. | |
| 2010/0204346 A1 | 8/2010 | Okuma et al. | |
| 2011/0275138 A1 | 11/2011 | Maruta et al. | |
| 2013/0316416 A1 | 11/2013 | Stephanopoulos et al. | |
| 2014/0186925 A1 | 7/2014 | Izumori et al. | |

FOREIGN PATENT DOCUMENTS

| | | |
|---|---|---|
| CN | 100577793 | 1/2010 |
| CN | 102373230 | 3/2012 |
| CN | 103131721 | 6/2013 |
| EP | 0592202 | 4/1994 |
| KR | 100832339 | 5/2008 |
| KR | 20110041910 | 4/2011 |
| KR | 101106253 | 1/2012 |
| KR | 1020090098938 | 1/2012 |
| WO | 2006129954 | 12/2006 |
| WO | 2006134374 | 12/2006 |
| WO | 2007058086 | 5/2007 |
| WO | 2011040708 | 4/2011 |
| WO | 2014025235 | 2/2014 |
| WO | 2014049373 | 4/2014 |

OTHER PUBLICATIONS

Jia et al., "Properties of D-allulose 3-epimerase mined from Novibacillus thermophilus and its application to synthesis of D-allulose", Enzyme Microb. Technol. 148:109816, 2021, 9 pages (Year: 2021).*
Notice of Allowance and Fee(s) Due issued in U.S. Appl. No. 14/431,549; dated Jun. 16, 2017, pp. 1-13.
Notice of Allowance and Fee(s) Due issued in U.S. Appl. No. 15/639,214; dated Feb. 14, 2019, pp. 1-9.
Office Action issued in U.S. Appl. No. 14/431,549; dated Mar. 1, 2016, pp. 1-26.
Office Action issued in U.S. Appl. No. 14/431,549; dated Dec. 20, 2016, pp. 1-13.
Office Action issued in U.S. Appl. No. 15/639,214; dated Oct. 15, 2018, pp. 1-29.

(Continued)

*Primary Examiner* — David Steadman
(74) *Attorney, Agent, or Firm* — McDonnell Boehnen Hulbert & Berghoff LLP

(57) ABSTRACT

The disclosure provides methods of manufacturing products comprising allulose produced by contacting a protein having allulose 3-epimerase activity with a fructose substrate under conditions such that the fructose substrate is converted into allulose. The disclosure also provides methods of manufacturing products comprising allulose produced by providing a vector comprising a nucleic acid molecule having a polynucleotide sequence encoding a protein having allulose 3-epimerase activity.

23 Claims, 10 Drawing Sheets

Specification includes a Sequence Listing.

(56) References Cited

OTHER PUBLICATIONS

Oh et al., "Increase in D-tagatose Protein Production Rate by Site-directed Mutagenesis of L-arabinose Isomerase from Geobacillus thermodenitrificans", Biotechnol. Letters 28, 2006—pp. 145-149.
Oh, "Tagatose: properties, applications, and biotechnological processes," Appl. Microbiol. Biotechnol. 76: 1-8 (2007).
Oshima et al., "Psicose Contents in Various Food Products and its Origin", Food Sc. Technol. Res., vol. 2, 2006—pp. 137-143.
Qing-Chao et al., Cloning, Express, Purification and Characterization of D-Tagatose-3-epimerase from Clostridium scindens ATCC 35704, Food and Fermentation Industries, 2011, vol. 37, No. 8—pp. 6-10.
Response to Office Action dated Dec. 20, 2016 filed Mar. 17, 2017 in U.S. Appl. No. 14/431,549; pp. 1-17.
Response to Office Action dated Oct. 15, 2018 filed Jan. 11, 2019 in U.S. Appl. No. 15/639,214; pp. 1-23.
Sambrook et al., "Molecular Cloning: A Laboratory Manual", 3rd edition, vol. 2, 10.47-10.48—3 pages, 2001.
Stemmer, W., "Dna Shuffling by Random Fragmentation and Reassembly: In Vitro Recombination for Molecular Evolution", Proc. Natl. Acad. Sci. USA, vol. 91, Oct. 1994—pp. 10747-10751.
Struhl, K., "Synthesizing Proteins In Vitro by Transcription of Cloned Genes", Current Protocols in Molecular Biology, Supplement 48, 1998—pp. 1Q .17.1-10.17.5.
Terpe, K., "Overview of Tag Protein Fusions: From Molecular and Biochemical Fundamentals to Commercial Systems", Appl. Microbiol. Biotechnol, 2003, 60—pp. 523-533.
Third Party Observations for PCT/GB2013/052531, dated Oct. 1, 2014—11 pages.
Uniprot, UniParc—UPI00020C8EAO (https://www.uniprol.org/uniparc/UPI00020C8EAO; accessed Apr. 8, 2020, pages (1-2).
Wagner et al., "Practical Aspects of Integrated Operation of Biotransformation and SMB Separation for Fine Chemical Synthesis", Org. Process Res. Dev., 2012, 16—pp. 323-330.
Yoshida et al., "Crystal Structures of D-Tagatose 3-Epimerase from Pseudomonas cichorii and its Complexes with D-Tagatose and D-Fructose", Journal of Molecular Biology, 2007, vol. 374—pp. 443-453.
Yoshida et al., "Purification, Crystallization and Preliminary X-ray Diffraction Studies of D-tagatose 3-epimerase from Pseudomonas cichorii", Acta Crystallographica Section F, 2007, No. F63—pp. 123-125.
Zhang et al., "Characterization of D-tagatose 3-epimerase from Rhodobacter sphaeroides that Converts D-fructose into 0-psicose", Biotechnology Letters, vol. 31, 2009—pp. 857-862.
Zhang et al., "Characterization of a Metal-dependent d-Psicose 3-epimerase from a Novel Strain, *Desmospora* sp. 8437," J. Agric. Food Chem., vol. 61, 2013—pp. 11468-11476.
Zhang et al., "Propagated Perturbations from a Peripheral Mutation Show Interactions Supporting WW Domain Thermostability," Structure 26: 147 4-1485, (2018).
Zhu et al., "Overexpression of D-psicose 3-epimerase from *Ruminococcus* sp. in *Escherichia* and its Potential Application in D-psicose Production", Biotechnology Letters, vol. 34, 2012—pp. 1901-1906.
IUBMB Enzyme Nomenclature EC 5.1.3.31, D-tagatose 3-epimerase, Jun. 8, 2017—1 page.
Accession No. BONGC3, putative uncharacterized protein, UniProt (online), Apr. 8, 2008, retrieved Apr. 20, 2017—2 pages.
Accession No. COCOP1, putative uncharacterized protein, UniProt, (online), May 5, 2009, retrieved Apr. 20, 2017—2 pages.
Advisory Action before the Filing of an Appeal Brief issued in U.S. Appl. No. 14/431,549; dated Oct. 25, 2016, pp. 1-11.
Altschul et al., BLAST algorithm version 2.2.2, 1997, URL http://www.ncbi.nlm.nih.gov/blast, retrieved Apr. 21, 2015—2 pages.
Altschul et al., "Gapped BLAST and PSI-BLAST: A New Generation of Protein Database Search Programs", Nucleic Acids Research, 1997, vol. 25, No. 17—pp. 3389-3402.
Amendment filed Jul. 1, 2016 in U.S. Appl. No. 14/431,549; pp. 1-14.
Amendment filed Nov. 11, 2016 in U.S. Appl. No. 14/431,549; pp. 1-13.
Amendment under 37 C.F.R. § 1.116 filed Oct. 10, 2016 in U.S. Appl. No. 14/431,549; pp. 1-10.
Applicant-Initialed Interview Summary issued in U.S. Appl. No. 14/431,549; dated Sep. 16, 2016, pp. 1-4.
Bai et al., "Bioconversion of D-fructose to D-allose by Novel Isomerases", Chinese Journal of Biotechnology, Apr. 25, 2012, 28(4)—pp. 457-465.
Binkley, W., "The Fate of Cane Juice Simple Sugars During Molasses Formation", The International Sugar Journal, Apr. 1963—pp. 105-106.
Bornscheuer et al., "Improved Biocatalysts by Directed Evolution and Rational Protein Design", Curr. Opin. Chem. Biol., 5, 2001—pp. 137-143.
Chan et al., "Crystal Structures of D-psicose 3-epimerase from Clostridium cellulolyticum H10 and its Complex with Ketohexose Sugars", Protein & Cell, vol. 3, No. 2, Feb. 1, 2012, Springer Asia, Beijing, CN—pp. 123-131.
Choi et al., "Improvement in the Thermostability of D-Psicose 3-Epimerase from Agrobacterium tumefaciens by Random and Site-Directed Mutagenesis", Applied and Environmental Microbiology, Oct. 2011, vol. 77, No. 20—pp. 7316-7320.
Chu et al., "Cloning, Expression and Characterization of Closteridium cellulolyticum D-Tagatose 3-Epimerase", Journal of Food Science and Biotechnology, Mar. 2011, vol. 30, No. 2—pp. 283-284.
Database UniProt [Online] Apr. 8, 2008, XP002720129, retrieved from the EBI Accession No. UNIPROT:BONGC3, database accession No. BONGC3—1 page.
Database UniProt [Online] May 5, 2009, XP002720130, retrieved from the EBI Accession No. UNIPROT:COCOP1, database accession No. COCOP1—1 page.
Database UniProt [Online] May 16, 2012, XP002717375, retrieved from the EBI Accession No. UNIPROT:F5SL39, database accession No. F5SL39—1 page.
Genbank:BAA24429.1 (1997); D-Tagatose 3-epimerase [Pseudomonas cichorii]—1 page.
Great Britain Search Report for Great Britain Application No. GB1220554.8, dated Mar. 18, 2013—5 pages.
Examiner-Initialed Interview Summary issued in U.S. Appl. No. 14/431,549; date of interview: Oct. 20, 2016, p. 1.
Examiner-Initialed Interview Summary issued in U.S. Appl. No. 15/639,214; date of interview: Oct. 9, 2018, p. 1.
Examiner-Initialed Interview Summary issued in U.S. Appl. No. 15/639,214; date of interview: Feb. 6, 2019, p. 1.
Final Office Action issued in U.S. Appl. No. 14/431,549; dated Jul. 12, 2016, pp. 1-19.
Iida et al., "Failure of D-psicose Absorbed in the Small Intestine to Metabolize into Energy and its Low Large Intestinal Fermentability in Humans", Metabolism Clinical and Experimental, vol. 59, 2010—pp. 206-214.
International Preliminary Report on Patentability for International Application No. PCT/GB2013/052531, dated Mar. 31, 2015—13 pages.
International Search Report and Written Opinion for International Application No. PCT/GB2013/052531, dated Feb. 25, 2014—8 pages.
Itoh et al., "Preparation of d-psicose from d-fructose by immobilized d-tagatose 3-epimerase," Journal of rermentation and Bioengineering, 1995, pp. 101-103, vol. 80, issue 1, Elsevier BV.
Itoh et al., "Purification and Characterization of D-Tagatose 3-Epimerase from *Pseudomonas* sp. ST-24," Biosci. Biotech. Biochem. 1994, 58(12) pp. 2168-2171.
Kim et al., "Characterization of and Agrobacterium tumefaciens D-psicose 3-epimerase that Converts D-Fructose to D-Psicose", Applied and Environmental Microbiology, Feb. 2006, vol. 72, No. 2—pp. 981-985.
Kim et al., "Crystal Structure of D-Psicose 3-Epimerase from Agrobacterium tumefaciens and its Complex with True Substrate D-Fructose: A Pivotal Role of Metal in Catalysis, an Active Site for

(56) References Cited

OTHER PUBLICATIONS the Non-phosphorylated Substrate, and its Conformational Changes", Journal of Molecular Biology, 2006, vol. 361—pp. 920-931.
Kim et al., "Mutational Analysis of the Active Sire Residues of a D-psicose 3-epimerase from Agrobacterium tumefaciens", Biotechnology Letters, 201 O. vol. 32—pp. 261-268, 2010.
Kim et al., "Roles of lle66 ano Ala 107 of D-psicose 3-epimerase from Agrobacterium turnefaciens in Binding 06 of its Substrate, D-fructose", Biotechnology Letters, vol. 32, 2010—pp. 113-118.
Lim et al., "Microbial Metabolism and Biotechnological Production of D-allose", Appl. Microbiol. Biotechnol., 2011, 91—pp. 229-235.
Luger et al., "Carbohydrates in Stream Treated Coffee", ASIC, 16th Colloque, Kyoto, 1995—pp. 366-371.
Meziere et al., "In vivo T Helper Cell Response to Retro-inverso Peptidomimetics", The Journal of Immunology, Oct. 1, 1997, vol. 159, No. 7—pp. 3230-3237 (abstract only).
Ming, "11. Biological aspects of metal enolates," The Chemistry of Metal Enolates, p. 629 (John Wiley & Sons, 2009).
Mu et al., "Characterization of a Novel D-tagatose 3-epimerase from Clostridium sciudens ATCC 35704", Journal of Biotechnology, vol. 150S, Nov. 1, 2010—pp. S536-S537 (Special Abstract).
Mu et al., "Cloning, Expression, and Characterization of a D-Psicose 3-Epimerase from Clostridium cellulolyticum H10", Journal of Agricultural and Food Chemistry, vol. 59, 2011—pp. 7785-7792.
Mu et al., "Recent Advances on Applications and Biotechnological Production of D-psicose", Applied Microbiology and Biotechnology, Jun. 2012, vol. 94, No. 6—pp. 1461-1467 (abstract only).
Muzny, D.et al, GenBank, D-tagatose 3-epimerase [*Desmospora* sp. 8437], dated Aug. 27, 2018, downloaded from the internet at https://www.ncbi.nlm.nih.gov/protein/332967973, 2 pages.
NCBI Accession No. NC_011898.1 (2009), Clostridium Cellulolyticum H10, Complete Geonome—1 page.
NCBI Accession No. NP_535228.1 (2001 ), D-tagatose 3-epimerase (Agrobacterium tumefaciens str. C58)—1 page.
NCBI Accession No. WP_009711885.1 (2013), Dolichol Monophosphate Mannose Synthase (*Desmospora* sp. 8437)—1 page.
NCB1 Accession No. WP_020816056.1 (2013), Dolichol Monophosphate Mannose Synthase (Clostridium papyrosolvens)—1 page.
NCBI Accession No. YP_002505284 (2009), Xylose Isomerase (Clostridium cellulolyticum H10)—1 page.
NCBI Accession No. ZP_02432281.1 (2007), Hypothetical Protein CLOSCI_02526 (Clostridium scindens ATCC 35704)—2 pages.
NCB1 Accession No. ZP_03778576.1 (2009), Hypothetical Protein CLOHYLEM 05645 (Clostridium hylemonae DSM 15053)—1 page.
NCB1 Accession No. ZP_04858451.1 (2009), Conserved Hypothetical Protein (*Ruminococcus* sp. 5_ 1_39B_FAA)—1 page.
NCBI Accession No. ZP 08466075.1 (2011), D-tagatose 3-epimerase (*Desmospora* sp. 8437)—1 page.

\* cited by examiner

Clostridium scindens Psicose-3-Epimerase (SEQ ID NO : 2)
MNRIGIFMNFWVKNWDADHVKYIKKVSGLGFDILEFQAQALLEMDKSRMDEVRQAAKDNGIELTYSLGLN
PKYDVASPDAKVREGGIEYLKRIVERIGYMEGKLLSGVNYAGWGSPDYIVDDKSEIVEHSIESVRQVIKT
AEDYDVTYCVEVVNRFEGIVMNTAKEAIEYVKQIDSDKIGILLDTYHMNIEEGSIGDAIRSVGGYLKNFH
TGENNRVVPGKGHLDWDEIFGALHDIDYQGRIVSEPFVQMGGEVARDIKVWRDLVEDPSEEVLDEEARFL
LNFEKDMIRKHYGIA

FIG. 1

Clostridium hylemonae Psicose - 3 - Epimerase (SEQ ID NO : 4)
MKHGIYYAYWEQEWAADYKRYVEKVAKLGFDILEIGAGPLPEYAEQDVKELKKCAQDNGITLTAGYGPTF
NHNIGSSDAGVREEALEWYKRLFEVLAELDIHLIGGALYSYWPVDFANADKTEDWKWSVEGMQRLAPAAA
KYDINGMEVLNRFESHILNTAEEGVKFVEEVGMDNVKVMLDTFHMNIEEQSIGGAIRRAGKLLGHFHTG
ECNRMVPGKGRIPWREIGDALRDIGYDGTAVMEPFVRMGGQVGADIKVWRDISRGADEAQLDDDARRALE
FQRYMLEWK

FIG. 2

Desmospora sp. Psicose-3-Epimerase (SEQ ID NO : 6)
MKYGVYFAYWEDSWDVDFEKYVRKVKKLGFDILEVAALGLVNLPEEKLERLKQLAEQHDIILTAGIGLPK
EYDVSSTDKKVRRNGISFMKKVMDAMHQAGIHRIGGTVYSYWPVDYSCSFDKPAVRKHSIESVRELAEYA
RQYNITLLIETLNRFEQFLLNDAEEEAVAYVKEVDEPNVKVMLDTFHMNIEEDHIADAIRYTGDHLGQLHI
GEANRKVPGKGSMPWTEIGQALKDIRYDGYVVMEPFIKTGGQVGRDIKLWRDLSGNATEEQLDRELAESL
EFVKAAFGE

FIG. 3

Clostridium cellulolyticum Psicose-3-Epimerase (SEQ ID NO : 8)
MKHGIYYAYWEQEWEADYKYYIEKVAKLGFDILE1AASPLPFYSDIQINELKACAHGNGITLTVGHGPSA
EQNLSSPDPDIRKNAKAFYTDLLKRLYKLDVHLIGGALYSYWPIDYTKTIDKKGDWERSVESVREVAKVA
EACGVDFCLEVLNRFENYLINTAQEGVDFVKQVDHNNVKVMLDTFHMNIEEDSIGGAIRTAGSYLGHLHT
GECNRKVPGRGRIPWVEIGEALADIGYNGSVVMEPFVRMGGTVGSNIKVWRDISNGADEKMLDREAQAAL
DFSRYVLECHKHS

FIG. 4

Psicose-3-Epimerase Clostridium cellulolyticum (SEQ ID NO 8)
Psicose-3-Epimerase Clostridium hylemonae (SEQ ID NO: 4)
Psicose-3-Epimerase Agrobacterium tumefaciens (SEQ ID NO: 14)
Psicose-3-Epimerase Desmospora sp. (SEQ ID NO: 6)
Tagatose-3-Epimerase Psuedomonas cichorii (SEQ ID NO: 15)
Psicose-3-Epimerase Clostridium scindens (SEQ ID NO: 2)

```
-MKH IYYAY EQE EADYKYYIEKVAK   IL IAASPLPFYSDIQIN
-MKH IYYAY EQE AADYKRYVEKVAK   IL IGAGPLPEYAEQDVK
-MKH IYYSY EHE SAKFGPYIEKVAK   II VAAHHINEYSDAELA
-MKY VYFAY EDS DVDFEKYVRKVKK   IL VAALGLVNLPEEKLE
MNKV MFYTY STE MVDFPATAKRIAG   LM ISLGEFHNLSDAKKR
MNRI IFMNF VKN DADHVKYIKKVSG   IL FQAQALLEMDKSRMD
      :*::  :*    .*  ...    .::  ****::*.     :   :

ELKAC HGNGITLTVGH PSAEQNLS P PDI KNAKAFYTDLLKRLYKL
ELKKC QDNGITLTAGY PTFNHNIG S AGV EEALEWYKRLFEVLAEL
TIRKS KDNGIILTAGI PSKTKNLS E AAV AAGKAFFERTLSNVAKL
RLKQL EQHDIILTAGI LPKEYDVS T KKV RNGISFMKKVMDAMHQA
ELKAV DDLGLTVMCCI LKSEYDFA P KSV DAGTEYVKRLLDDCHLL
EVRQA KDNGIELTYLS LNPKYDVA P AKV EGGIEYLKRIVERIGYM
 ::    *.  .: :   *         :..* *  :*   .  :   ..

DVHLIG ALYSY PIDYTKTID- KGDWERSV SVREVAKV EACGVDFC
DIHLIG ALYSY PVDFAN-AD- TEDWKWSV GMQRLAPA AKYDINLG
DIHTIG ALHSY PIDYSQPVD- AGDYARGV GINGIADF NDLGINLC
GIHRIG TVYSY PVDYSCSFD- PAVRKHSI SVRELAEY RQYNITLL
GAPVFA LTFCA PQSPPLDMKD RPYVDRAI SVRRVIKV EDYGIIYA
EGKLLS VNYAG G-SPDYIVDD SEIVEHSI SVRQVIKT EDYDVTYC
 :.*   ..  *    .      .  *     .:*.:: .    *  .:

L VL   NYLI T Q GVDFVKQVDHNNVKVM  F     DSIGG
M VL   SHIL T E GVKFVEEVGMDNVKVM  F     QSIGG
I VL   NHVL T A GVAFVKDVGKNNVKVM  F     DSFGD
I TL   QFLL D E AVAYVKEVDEPNVKVM  F     DHIAD
L VV   QWLC D K AIAFADAVDSPACKVQ  F     TSFRD
V VV   GIVM T K AIEYVRQIDSDKIGIL  Y     GSIGD
:*.:****   :  *   *.:  :.. :.      : ***:******   :  .**

RTAGSYLGHL T  C KV R RIP V GE AD G N SVVM   VR
RRAGKLLGHF T  C MV K RIP P GD RD G D TAVM   VR
RTAGPLLGHF T  S RV K RMP H GL RD N T AVIM   VK
RYTGDHLGQL I  A KV K SMP T GQ KD R D YVVM   IK
LACKGKMGHF L  A LP E RLP D FG KE G D TIVM   MR
RSVGGYLKNF T  N VV K HLD D FG HD D Q RIVS   VQ
      :  ::  **  **    **.*. ;    *   **    **  :*    *    *     :   ***;;

M  TVGSNIKV   ISNGADEKML REAQAA D SRYVLECHKHS--
M  QVGADIKV   ISRGADEAQL DDARPA E QRYMLEWK-----
T  TIGSDIKV   LSGGADIAKM EDARNA A SRFVLGG-----
T  QVGRDIKL   LSGNATEEQL RELAES E VKAAFGE-----
K  SVSRAVGV   MSNGATDEEM ERARRS Q VRDKLA------
M  EVARDIKV   LVEDPSEEVL EEARFL N EKDMIRKHYGIA
**  :.   :  :***:   . .    :*       *  :  :
```

FIG. 5

Clostridium cellulolyticum
(Optimized Sequence Length:897, GC%:51.61) (SEQ ID NO: 7)
CATATG
AAGCACGGCATCTATTACGCCTATTGGGAACAAGAATGGGAAGCAGACTACAAGTATTACATCGAAAAGGTTGCG
AAGCTGGGTTTTGATATTCTGGAAATCGCGGCCTCACCGCTGCCGTTTTATTCGGACATTCAGATCAATGAACTG
AAAGCGTGCGCGCATGGCAACGGTATTACCCTGACGGTGGGCCACGGTCCGAGCGCGGAACAAAATCTGAGCAGC
CCGGACCCGGACATCCGTAAAAACGCAAAGGCTTTCTATACCGATCTGCTGAAACGCCTGTACAAGCTGGACGTT
CATCTGATTGGCGGTGCCCTGTATTCTTACTGGCCGATCGATTACACCAAGACGATCGATAAGAAGGGCGACTGG
GAACGTAGTGTTGAATCCGTCCGCGAAGTGGCCAAGGTTGCGGAAGCCTGCGGTGTCGATTTTGTCTGGAAGTG
CTGAACCGTTTCGAAAATTACCTGATTAACACCGCACAGGAAGGCGTCGATTTTGTGAAACAAGTTGACCATAAC
AATGTCAAGGTGATGCTGGATACGTTCCACATGAATATCGAAGAAGACAGTATTGGCGGTGCGATCCGTACCGCC
GGCTCCTATCTGGGTCATCTGCACACGGGCGAATGCAATCGCAAAGTTCCGGGCCGTGGTCGCATTCCGTGGGTC
GAAATCGGTGAAGCACTGGCTGATATTGGCTACAACGGTTCAGTGGTTATGGAACCGTTTGTTCGTATGGGCGGC
ACCGTCGGCAGCAATATTAAAGTGTGGCGCGATATCTCTAACGGTGCAGATGAAAAGATGCTGGACCGTGAAGCT
CAGGCAGCTCTGGACTTCTCACGCTACGTGCTGGAATGTCATAAACACTCGTAA
AGATCTGGATCC
DNA Alignment (Optimized Region) (Upper: SEQ ID NO: 7; Lower: SEQ ID NO:12
Optimized 7     AAGCACGGCATCTATTACGCCTATTGGGAACAAGAATGGGAAGCAGACTACAAGTATTAC
Original  7     AAACATGGTATATACTACGCATATTGGGAACAAGAATGGGAAGCTGATTACAAATACTAT
Optimized 67    ATCGAAAAGGTTGCGAAGCTGGGTTTTGATATTCTGGAAATCGCGGCCTCACCGCTGCCG
Original  67    ATTGAGAAGGTTGCAAAGCTTGGTTTTGATATTCTAGAGATTGCAGCTTCACCGCTACCT
Optimized 127   TTTTATTCGGACATTCAGATCAATGAACTGAAAGCGTGCGCGCATGGCAACGGTATTACC
Original  127   TTTTACAGTGACATTCAGATTAATGAGCTCAAGGCATGTGCCCATGGCAATGGAATTACA
Optimized 187   CTGACGGTGGGCCACGGTCCGAGCGCGGAACAAAATCTGAGCAGCCCGGACCCGGACATC
Original  187   CTTACGGTAGGCCATGGGCCTAGTGCAGAACAAAACCTGTCTTCTCCCGACCCCGATATT
Optimized 247   CGTAAAAACGCAAAGGCTTTCTATACCGATCTGCTGAAACGCCTGTACAAGCTGGACGTT
Original  247   CGCAAAAATGCTAAAGCTTTTTATACCGATTTACTCAAACGACTTTACAAGCTGGATGTA
Optimized 307   CATCTGATTGGCGGTGCCCTGTATTCTTACTGGCCGATCGATTACACCAAGACGATCGAT
Original  307   CATTTGATAGGTGGGGCTTTATATTCTTATTGGCCGATAGATTACACAAAGACAATTGAT
Optimized 367   AAGAAGGGCGACTGGGAACGTAGTGTTGAATCCGTCCGCGAAGTGGCCAAGGTTGCGGAA
Original  367   AAAAAAGGCGATTGGGAACGCAGCGTTGAAAGTGTTCGAGAAGTTGCTAAGGTGGCCGAA
Optimized 427   GCCTGCGGTGTCGATTTTGTCTGGAAGTGCTGAACCGTTTCGAAAATTACCTGATTAAC
Original  427   GCCTGTGGAGTGGATTTCTGCCTAGAGGTTCTTAATAGATTTGAGAATTATTTAATTAAC
Optimized 487   ACCGCACAGGAAGGCGTCGATTTTGTGAAACAAGTTGACCATAACAATGTCAAGGTGATG
Original  487   ACAGCACAAGAGGGTGTAGATTTTGTAAAACAGGTTGACCATAACAATGTAAAGGTAATG
Optimized 547   CTGGATACGTTCCACATGAATATCGAAGAAGACAGTATTGGCGGTGCGATCCGTACCGCC
Original  547   CTTGATACCTTCCATATGAATATTGAGGAAGATAGTATCGGAGGTGCAATCAGGACTGCG
Optimized 607   GGCTCCTATCTGGGTCATCTGCACACGGGCGAATGCAATCGCAAAGTTCCGGGCCGTGGT
Original  607   GGCTCTTACTTGGGACATTTACACACTGGCGAATGTAATCGTAAAGTTCCCGGCAGAGGA
Optimized 667   CGCATTCCGTGGGTCGAAATCGGTGAAGCACTGGCTGATATTGGCTACAACGGTTCAGTG
Original  667   AGAATTCCATGGGTAGAAATTGGTGAGGCTCTTGCTGACATAGGTTATAACGGTAGTGTT
Optimized 727   GTTATGGAACCGTTTGTTCGTATGGGCGGCACCGTCGGCAGCAATATTAAAGTGTGGCGC
Original  727   GTTATGGAACCTTTTGTTAGAATGGGCGGAACTGTCGGATCTAATATTAAGGTTTGGCGT
Optimized 787   GATATCTCTAACGGTGCAGATGAAAAGATGCTGGACCGTGAAGCTCAGGCAGCTCTGGAC
Original  787   GACATTAGTAACGGTGCAGATGAGAAAATGCTGGATAGAGAAGCACAGGCCGCACTTGAT
Optimized 847   TTCTCACGCTACGTGCTGGAATGTCATAAACACTCGTAA
Original  847   TTCTCCAGATATGTATTAGAATGTCATAAACACTCCTGA

FIG. 7

Desmospora sp. (SEQ ID NO: 5)
CATATG
AAATACGGTGTCTACTTTGCTTACTGGGAAGATTCGTGGGATGTTGACTTTGAAAAATACGTTCGCAAGGTGAAA
AAACTGGGCTTTGATATTCTGGAAGTTGCAGCACTGGGTCTGGTCAACCTGCCGGAAGAAAAACTGGAACGTCTG
AAGCAGCTGGCGGAACAACATGACATTATCCTGACCGCCGGCATTGGTCTGCCGAAAGAATATGATGTCAGCTCT
ACGGACAAAAAAGTGCGTCGCAATGGCATCTCCTTTATGAAAAAGGTTATGGATGCAATGCATCAGGCTGGTATT
CACCGTATTGGCGGCACCGTGTATAGCTACTGGCCGGTTGATTACAGTTGCTCCTTCGACAAACCGGCGGTTCGC
AAGCACTCAATTGAATCGGTCCGTGAACTGGCGGAATATGCCCGCCAGTACAACATTACCCTGCTGATCGAAACG
CTGAACCGCTTTGAACAATTCCTGCTGAATGATGCCGAAGAAGCGGTTGCCTATGTCAAAGAAGTGGATGAACCG
AACGTCAAGGTGATGCTGGACACCTTCCACATGAACATCGAAGAAGATCACATCGCAGACGCTATCCGTTACACG
GGCGATCATCTGGGTCAGCTGCACATCGGCGAAGCCAACCGCAAAGTGCCGGGCAAGGGTAGTATGCCGTGGACC
GAAATTGGCCAAGCACTGAAAGATATCCGTTATGACGGTTACGTGGTTATGGAACCGTTCATTAAAACCGGCGGT
CAGGTTGGCCGTGATATCAAACTGTGGCGCGACCTGAGCGGTAATGCAACGGAAGAACAACTGGATCGCGAACTG
GCTGAATCTCTGGAATTTGTGAAAGCAGCTTTCGGTGAATAA
AGATCTGGATCC DNA Alignment (Optimized Region) (Upper: SEQ ID NO: 5; Lower: SEQ ID NO:11

Optimized 7    AAATACGGTGTCTACTTTGCTTACTGGGAAGATTCGTGGGATGTTGACTTTGAAAAATAC
Original 7     AAATACGGTGTCTATTTCGCTTACTGGGAAGACTCGTGGGATGTGGATTTCGAGAAGTAC
Optimized 67   GTTCGCAAGGTGAAAAAACTGGGCTTTGATATTCTGGAAGTTGCAGCACTGGGTCTGGTC
Original 67    GTGCGGAAAGTGAAAAAGTTGGGCTTCGACATCCTCGAAGTGGCGGCATTGGGTCTCGTC
Optimized 127  AACCTGCCGGAAGAAAAACTGGAACGTCTGAAGCAGCTGGCGGAACAACATGACATTATC
Original 127   AACCTTCCGGAGGAGAAACTGGAGCGGCTGAAACAACTCGCCGAACAGCACGATATCATC
Optimized 187  CTGACCGCCGGCATTGGTCTGCCGAAAGAATATGATGTCAGCTCTACGGACAAAAAAGTG
Original 187   CTGACGGCCGGGATCGGCCTGCCAAAGGAATACGATGTCTCGTCAACTGACAAAAAGGTG
Optimized 247  CGTCGCAATGGCATCTCCTTTATGAAAAAGGTTATGGATGCAATGCATCAGGCTGGTATT
Original 247   CGCCGGAACGGCATCTCCTTCATGAAGAAAGTGATGGACGCGATGCATCAGGCCGGCATC
Optimized 307  CACCGTATTGGCGGCACCGTGTATAGCTACTGGCCGGTTGATTACAGTTGCTCCTTCGAC
Original 307   CACCGGATCGGCGGCACGGTCTACTCGTATTGGCCGGTTGACTACAGTTGCTCCTTCGAC
Optimized 367  AAACCGGCGGTTCGCAAGCACTCAATTGAATCGGTCCGTGAACTGGCGGAATATGCCCGC
Original 367   AAGCCGGCCGTAAGGAAGCACAGCATCGAAAGCGTCAGAGAGCTGGCGGAGTACGCACGG
Optimized 427  CAGTACAACATTACCCTGCTGATCGAAACGCTGAACCGCTTTGAACAATTCCTGCTGAAT
Original 427   CAGTACAACATCACACTCCTCATCGAAACGCTCAACCGGTTTGAGCAGTTTCTCCTGAAC
Optimized 487  GATGCCGAAGAAGCGGTTGCCTATGTCAAAGAAGTGGATGAACCGAACGTCAAGGTGATG
Original 487   GACGCGGAGGAAGCAGTCGCCTATGTGAAGGAAGTGGACGAGCCGAATGTGAAAGTCATG
Optimized 547  CTGGACACCTTCCACATGAACATCGAAGAAGATCACATCGCAGACGCTATCCGTTACACG
Original 547   CTCGACACATTCCACATGAACATCGAGGAAGACCACATTGCCGATGCCATCCGCTACACC
Optimized 607  GGCGATCATCTGGGTCAGCTGCACATCGGCGAAGCCAACCGCAAAGTGCCGGGCAAGGGT
Original 607   GGTGACCACCTCGGCCAACTGCACATCGGCGAAGCGAATCGGAAAGTCCCGGGCAAGGGT
Optimized 667  AGTATGCCGTGGACCGAAATTGGCCAAGCACTGAAAGATATCCGTTATGACGGTTACGTG
Original 667   TCGATGCCTTGGACAGAAATCGGACAGGCGCTGAAAGACATTCGCTACGATGGCTACGTT
Optimized 727  GTTATGGAACCGTTCATTAAAACCGGCGGTCAGGTTGGCCGTGATATCAAACTGTGGCGC
Original 727   GTCATGGAACCCTTCATCAAAACCGGCGGACAGGTCGGCCGGGACATCAAGCTCTGGCGC
Optimized 787  GACCTGAGCGGTAATGCAACGGAAGAACAACTGGATCGCGAACTGGCTGAATCTCTGGAA
Original 787   GATCTGTCGGGAATGCGACGGAGGAACAGTTGGACCGGGAGCTGGCAGAGTCGCTGGAA
Optimized 847  TTTGTGAAAGCAGCTTTCGGTGAATAA
Original 847   TTTGTGAAAGCGGCGTTCGGGGAGTAA

FIG. 8

Clostridium scindens
(Optimized Sequence Length:903, GC%:49.13) (SEQ ID NO: 1)
CATATG
AATCGTATTGGCATTTTTATGAATTTTTGGGTGAAGAACTGGGACGCTGACCACGTTAAGTACATCAAGAAGGTG
TCGGGCCTGGGCTTTGATATTCTGGAATTTCAGGCACAAGCTCTGCTGGAAATGGATAAATCTCGTATGGACGAA
GTGCGCCAGGCGGCCAAGGATAACGGCATTGAACTGACCTATTCTCTGGGTCTGAATCCGAAATACGATGTGGCA
AGTCCGGACGCTAAGGTTCGTGAAGGCGGTATCGAATATCTGAAACGTATTGTGGAACGCATCGGCTACATGGAA
GGCAAGCTGCTGTCAGGCGTTAACTATGCGGGCTGGGGTTCGCCGGATTACATTGTCGATGACAAAAGCGAAATT
GTGGAACATAGCATCGAAAGCGTGCGTCAGGTCATCAAAACCGCCGAAGATTATGACGTGACGTACTGCGTTGAA
GTGGTTAACCGCTTTGAAGGCATTGTTATGAATACCGCGAAAGAAGCCATTGAATATGTCAAACAAATCGATAGC
GACAAGATTGGTATCCTGCTGGATACGTACCACATGAACATCGAAGAAGGCAGTATTGGTGATGCGATCCGTTCC
GTTGGCGGTTATCTGAAAAATTTCCACACGGGCGAAAACAATCGCGTCGTGCCGGGCAAGGGTCATCTGGATTGG
GACGAAATTTTTGGCGCACTGCACGATATTGACTACCAGGGTCGCATCGTCTCCGAACCGTTCGTGCAAATGGGC
GGTGAAGTGGCTCGTGATATCAAAGTTTGGCGCGATCTGGTCGAAGACCCGAGCGAAGAAGTTCTGGATGAAGAA
GCGCGTTTTCTGCTGAATTTCGAAAAAGACATGATTCGCAAGCACTATGGTATCGCCTAA
AGATCTGGATCC DNA Alignment (Optimized Region) (Upper: SEQ ID NO: 1; Lower: SEQ ID NO: 9)
Optimized 7    AATCGTATTGGCATTTTTATGAATTTTTGGGTGAAGAACTGGGACGCTGACCACGTTAAG
Original 7     AACAGAATAGGAATATTTATGAATTTCTGGGTTAAGAACTGGGATGCAGATCATGTCAAG
Optimized 67   TACATCAAGAAGGTGTCGGGCCTGGGCTTTGATATTCTGGAATTTCAGGCACAAGCTCTG
Original 67    TATATTAAAAAGGTATCCGGCCTTGGATTTGATATTCTGGAATTCCAGGCCCAGGCGCTT
Optimized 127  CTGGAAATGGATAAATCTCGTATGGACGAAGTGCGCCAGGCGGCCAAGGATAACGGCATT
Original 127   CTGGAGATGGATAAGAGCAGGATGGATGAGGTCAGGCAGGCGGCAAAGGACAATGGAATC
Optimized 187  GAACTGACCTATTCTCTGGGTCTGAATCCGAAATACGATGTGGCAAGTCCGGACGCTAAG
Original 187   GAACTGACCTACAGCCTTGGGCTGAATCCTAAGTACGATGTCGCAAGCCCGGATGCAAAA
Optimized 247  GTTCGTGAAGGCGGTATCGAATATCTGAAACGTATTGTGGAACGCATCGGCTACATGGAA
Original 247   GTCAGGGAAGGCGGAATCGAATATCTGAAGCGGATCGTGGAGCGGATTGGATACATGGAA
Optimized 307  GGCAAGCTGCTGTCAGGCGTTAACTATGCGGGCTGGGGTTCGCCGGATTACATTGTCGAT
Original 307   GGAAAACTGCTTTCCGGAGTCAACTATGCCGGCTGGGGAAGCCCGGACTATATCGTGGAT
Optimized 367  GACAAAAGCGAAATTGTGGAACATAGCATCGAAAGCGTGCGTCAGGTCATCAAAACCGCC
Original 367   GACAAAAGCGAGATCGTGGAGCACAGCATCGAAAGCGTCCGCCAGGTCATTAAGACGGCA
Optimized 427  GAAGATTATGACGTGACGTACTGCGTTGAAGTGGTTAACCGCTTTGAAGGCATTGTTATG
Original 427   GAAGATTATGACGTGACTTACTGCGTGGAGGTCGTGAACCGGTTTGAGGGCATCGTGATG
Optimized 487  AATACCGCGAAAGAAGCCATTGAATATGTCAAACAAATCGATAGCGACAAGATTGGTATC
Original 487   AATACGGCAAAGGAAGCCATCGAGTACGTGAAGCAGATTGACAGTGATAAGATCGGAATC
Optimized 547  CTGCTGGATACGTACCACATGAACATCGAAGAAGGCAGTATTGGTGATGCGATCCGTTCC
Original 547   CTGCTGGATACCTATCATATGAACATCGAGGAAGGCTCTATAGGAGACGCCATCCGATCT
Optimized 607  GTTGGCGGTTATCTGAAAAATTTCCACACGGGCGAAAACAATCGCGTCGTGCCGGGCAAG
Original 607   GTAGGCGGATATCTGAAGAACTTCCACACTGGAGAGAACAACCGGGTCGTTCCGGGGAAG
Optimized 667  GGTCATCTGGATTGGGACGAAATTTTTGGCGCACTGCACGATATTGACTACCAGGGTCGC
Original 667   GGGCACCTCGACTGGGATGAAATATTTGGAGCGCTCCATGATATCGATTATCAGGGAAGG
Optimized 727  ATCGTCTCCGAACCGTTCGTGCAAATGGGCGGTGAAGTGGCTCGTGATATCAAAGTTTGG
Original 727   ATCGTGTCAGAGCCGTTCGTCCAGATGGGCGGGGAAGTCGCAAGAGACATCAAGGTATGG
Optimized 787  CGCGATCTGGTCGAAGACCCGAGCGAAGAAGTTCTGGATGAAGAAGCGCGTTTTCTGCTG
Original 787   AGAGATCTGGTGGAAGATCCTTCAGAAGAAGTGCTGGATGAGGAGGCGCGCTTCCTTCTG
Optimized 847  AATTTCGAAAAAGACATGATTCGCAAGCACTATGGTATCGCCTAA
Original 847   AATTTTGAAAAGGATATGATCCGGAAGCACTATGGCATAGCGTAA

FIG. 9

Clostridium hylemonae
(Optimized Sequence Length:885, GC%:52.20) (SEQ ID NO: 3)
CATATG
AAACACGGTATCTATTACGCCTATTGGGAACAAGAATGGGCAGCAGACTACAAACGCTATGTGGAAAAAGTGGCA
AAACTGGGCTTCGATATTCTGGAAATCGGCGCCGGTCCGCTGCCGGAATATGCAGAACAGGACGTTAAAGAACTG
AAAAAGTGCGCTCAAGATAACGGCATTACCCTGACGGCGGGCTACGGTCCGACCTTTAACCATAATATCGGCAGC
TCTGATGCTGGTGTGCGTGAAGAAGCGCTGGAATGGTATAAACGCCTGTTCGAAGTTCTGGCCGAACTGGACATT
CACCTGATCGGCGGTGCACTGTATAGTTACTGGCCGGTCGATTTTGCTAACGCGGACAAAACGGAAGATTGGAAG
TGGTCCGTGGAGGGTATGCAGCGTCTGGCCCCGGCGGCGGCAAAATACGATATTAACCTGGGTATGGAAGTTCTG
AATCGCTTTGAATCACATATCCTGAATACCGCCGAAGAAGGCGTCAAATTCGTGGAAGAAGTTGGTATGGACAAC
GTGAAGGTTATGCTGGATACGTTCCACATGAATATTGAAGAACAATCGATTGGCGGTGCCATCCGTCGCGCAGGC
AAACTGCTGGGTCATTTTCACACCGGCGAATGTAATCGTATGGTGCCGGGCAAGGGTCGTATTCCGTGGCGCGAA
ATCGGTGACGCTCTGCGTGATATCGGCTACGACGGTACGGCAGTCATGGAACCGTTCGTGCGTATGGGTGGTCAG
GTTGGTGCAGATATTAAAGTCTGGCGTGACATCTCTCGCGGTGCCGATGAAGCACAGCTGGATGACGATGCTCGT
CGCGCGCTGGAATTTCAACGCTATATGCTGGAATGGAAGTAA
AGATCTGGATCC DNA Alignment (Optimized Region) (Upper: SEQ ID NO: 3; Lower: SEQ ID NO:10

Optimized 7    AAACACGGTATCTATTACGCCTATTGGGAACAAGAATGGGCAGCAGACTACAAACGCTAT
Original  7    AAACATGGTATCTATTATGCATACTGGGAACAAGAATGGGCGGCCGACTACAAGCGCTAT
Optimized 67   GTGGAAAAAGTGGCAAAACTGGGCTTCGATATTCTGGAAATCGGCGCCGGTCCGCTGCCG
Original  67   GTTGAAAAGGTGGCAAAGCTTGGGTTTGACATTCTGGAGATCGGCGCTGGGCCGCTGCCG
Optimized 127  GAATATGCAGAACAGGACGTTAAAGAACTGAAAAAGTGCGCTCAAGATAACGGCATTACC
Original  127  GAATACGCAGAGCAGGATGTGAAGGAACTGAAGAAATGTGCGCAGGACAATGGGATCACG
Optimized 187  CTGACGGCGGGCTACGGTCCGACCTTTAACCATAATATCGGCAGCTCTGATGCTGGTGTG
Original  187  CTGACGGCCGGATATGGTCCGACGTTCAACCACAATATCGGTTCTTCAGACGCCGGGGTA
Optimized 247  CGTGAAGAAGCGCTGGAATGGTATAAACGCCTGTTCGAAGTTCTGGCCGAACTGGACATT
Original  247  AGGGAAGAGGCGCTGGAATGGTATAAGAGGTTATTTGAAGTGCTGGCAGAGCTTGATATC
Optimized 307  CACCTGATCGGCGGTGCACTGTATAGTTACTGGCCGGTCGATTTTGCTAACGCGGACAAA
Original  307  CACCTGATCGGAGGGGCGCTCTATTCTTACTGGCCTGTCGATTTTGCAAACGCCGATAAA
Optimized 367  ACGGAAGATTGGAAGTGGTCCGTGGAGGGTATGCAGCGTCTGGCCCCGGCGGCGGCAAAA
Original  367  ACGGAAGACTGGAAGTGGAGTGTAGAGGGCATGCAGAGGCTGGCGCCGGCCGCGGCCAAA
Optimized 427  TACGATATTAACCTGGGTATGGAAGTTCTGAATCGCTTTGAATCACATATCCTGAATACC
Original  427  TATGACATCAACCTGGGCATGGAAGTTCTGAACCGGTTTGAGAGCCATATCCTGAATACA
Optimized 487  GCCGAAGAAGGCGTCAAATTCGTGGAAGAAGTTGGTATGGACAACGTGAAGGTTATGCTG
Original  487  GCCGAGGAAGGTGTGAAGTTTGTAGAGGAAGTCGGCATGGACAACGTAAAGGTCATGCTG
Optimized 547  GATACGTTCCACATGAATATTGAAGAACAATCGATTGGCGGTGCCATCCGTCGCGCAGGC
Original  547  GATACATTCCATATGAATATAGAAGAGCAAAGCATAGGCGGCGCGATCCGCCGGGCAGGA
Optimized 607  AAACTGCTGGGTCATTTTCACACCGGCGAATGTAATCGTATGGTGCCGGGCAAGGGTCGT
Original  607  AAACTGCTCGGGCATTTCCACACCGGAGAATGCAACCGCATGGTGCCCGGGAAGGGACGT
Optimized 667  ATTCCGTGGCGCGAAATCGGTGACGCTCTGCGTGATATCGGCTACGACGGTACGGCAGTC
Original  667  ATTCCATGGCGTGAGATAGGGGATGCTCTCCGTGATATCGGATATGACGGAACTGCTGTA
Optimized 727  ATGGAACCGTTCGTGCGTATGGGTGGTCAGGTTGGTGCAGATATTAAAGTCTGGCGTGAC
Original  727  ATGGAGCCGTTCGTTCGCATGGGAGGACAGGTCGGCGCTGATATCAAGGTGTGGAGAGAC
Optimized 787  ATCTCTCGCGGTGCCGATGAAGCACAGCTGGATGACGATGCTCGTCGCGCGCTGGAATTT
Original  787  ATAAGCCGTGGAGCAGACGAGGCACAGCTTGACGATGACGCGCGCCGTGCGCTGGAGTTC
Optimized 847  CAACGCTATATGCTGGAATGGAAGTAA
Original  847  CAGAGATATATGCTGGAGTGGAAGTAA

FIG. 10

```
MRYGIYYAYWEDSWDADFEKYVKKVKKLGFDIIEVAALGFVNLPEEKLETLRQLA
EQHDIILTAGYGLPKEYNVSSPDKKVRRNGISFMKKVLDAMHQLGIHRIGGTVFS
YWPVDYSCSFDKPAVRKHAIESVREVAEYARQYNITLAIEVLNRFEQFVLNDAEE
AIAYVKEVGEPNVKVMLDTFHMNIEEDHFADAIRYAGDLLGQLHIGEANRKVPGK
GSLPWTEIGQALKDIRYDGYVIMEPFVKTGGTVGRDVKLWRDMSGNATEEQLDRE
LAESLEFVRAAFGE (SEQ ID NO. 13)
```

FIG. 15

METHODS FOR MANUFACTURING A PRODUCT USING A 3-EPIMERASE

CROSS-REFERENCE TO RELATED APPLICATIONS

This application is a continuation of U.S. application Ser. No. 16/370,163, filed Mar. 29, 2019, now abandoned, which is a continuation of U.S. application Ser. No. 15/639,214, filed Jun. 30, 2017, now U.S. Pat. No. 10,294,469, issued May 21, 2019, which is a continuation of U.S. application Ser. No. 14/431,549, filed Mar. 26, 2015, now U.S. Pat. No. 9,725,707, issued Aug. 8, 2017, which is a national stage application under 35 U.S.C. § 371 of International Application No. PCT/GB2013/052531, filed Sep. 27, 2013, which claims priority from U.S. Provisional Application No. 61/706,338, filed Sep. 27, 2012, and United Kingdom (GB) Application No. 1220554.8, filed Nov. 15, 2012. The disclosures of each of these applications are incorporated herein by reference in their entirety for all purposes.

INCORPORATION BY REFERENCE OF SEQUENCE LISTING PROVIDED ELECTRONICALLY

This application contains a Sequence Listing submitted as an electronic text file named "Sequence Listing", having a of 41,441 bytes, which was created on Dec. 31, 2020. The information contained in this electronic file is hereby incorporated by reference in its entirety.

FIELD OF THE INVENTION

The present invention relates to a protein having ketose 3-epimerase activity and a nucleic acid molecule encoding said protein. The invention also relates to a vector and a host cell comprising the nucleic acid molecule. The invention also relates to a method of synthesising allulose using the protein and to allulose produced in such a manner.

BACKGROUND OF THE INVENTION

Allulose is a "zero-calorie" sweetener and has sweetness suggested to be similar to dextrose. It also has bulking and browning properties similar to those of other sugars. The primary target market for allulose is food and beverage manufacturers that currently use dextrose, fructose or HFCS in their products and that are looking to significantly reduce calories without significantly altering other properties imparted by the sugar component, for example, bulking, browning, texture and sweetness.

Allulose is not Generally Regarded As Safe (GRAS) in the United States but there is currently a GRAS notice pending (GRN400). Allulose is present in processed cane and beet molasses, steam treated coffee, wheat plant products and high fructose corn syrup. The typical total daily intake of allulose has been estimated to be greater than 0.2 grams per day. D-allulose is the C-3 epimer of D-fructose, and the structural difference between allulose and fructose results in allulose not being metabolized by the human body and thus having zero calories. Therefore, allulose is thought to be a promising candidate as a sweet bulking agent as it has no calories and is reported to be sweet while maintaining similar properties to typical monosaccharides.

Ketose-3-epimerases can interconvert fructose and allulose. U.S. Pat. No. 8,030,035 and PCT publication no. WO2011/040708 disclose that D-psicose (an alternative name for allulose) can be produced by reacting a protein derived from *Agrobacterium tumefaciens*, and having psicose 3-epimerase activity, with D-fructose.

US patent publication no. 2011/0275138 discloses a ketose 3-epimerase derived from a microorganism of the *Rhizobium* genus. This protein shows a high specificity to D- or L-ketopentose and D- or L-ketohexose, and especially to D-fructose and D-psicose. This document also discloses a process for producing ketoses by using the protein.

Korean patent no. 100832339 discloses a *Sinorhizobium* YB-58 strain which is capable of converting fructose into psicose (i.e. allulose), and a method of producing psicose using a fungus body of the *Sinorhizobium* YB-58 strain.

Korean patent application no. 1020090098938 discloses a method of producing psicose using *E. coli* wherein the *E. coli* expresses a polynucleotide encoding a psicose 3-epimerase.

The present invention seeks to provide an improvement in the production of allulose over existing technology. The present invention seeks to provide a ketose-3-epimerase with higher rates of conversion and volumetric productivity in a whole cell system than previously reported.

SUMMARY OF THE INVENTION

The present invention arises from the identification and characterisation of three ketose-3-epimerase enzymes, exemplary amino acid sequences of which are shown in SEQ. ID NOS: 2, 4 and 6. The ketose-3-epimerases may be used to convert fructose to allulose. These proteins had previously been identified as hypothetical proteins or as having tagatose epimerase activity. However, the present inventors have now surprisingly found that these enzymes have psicose-3-epimerase activity.

According to a first aspect of the present invention there is provided a protein comprising a polypeptide sequence having at least 70% sequence identity to SEQ ID NO: 2, SEQ ID NO: 4 or SEQ ID NO: 6, wherein the protein has ketose 3-epimerase activity.

Conveniently, the polypeptide sequence has at least 80%, 90%, 95% or 99% sequence identity, or has 100% sequence identity, to SEQ ID NO: 2, SEQ ID NO: 4 or SEQ ID NO: 6.

Advantageously, the polypeptide sequence comprises the sequence of SEQ ID NO: 13.

Preferably, the protein is immobilized on a solid substrate.

According to a second aspect of the present invention there is provided the use of a protein according to the first aspect of the invention for synthesizing allulose.

According to a third aspect of the present invention there is provided a nucleic acid molecule comprising a polynucleotide sequence encoding a protein according to the first aspect of the invention.

Advantageously, the nucleic acid molecule comprises a polynucleotide sequence which:
 i) has at least 70%, 80%, 90%, 95% or 99% sequence identity, or has 100% sequence identity, to SEQ ID NO: 5, SEQ ID NO: 1 or SEQ ID NO: 3; or
 ii) hybridizes under highly stringent conditions to a polynucleotide having a sequence complementary to the sequence set forth in SEQ ID NO: 5, SEQ ID NO: 1 or SEQ ID NO: 3.

According to a fourth aspect of the present invention there is provided a vector comprising a nucleic acid molecule according to the third aspect of the invention.

According to a fifth aspect of the present invention there is provided a host cell comprising a recombinant nucleic acid molecule according to the third aspect of the invention.

Conveniently, the host cell is a yeast, bacterium or other microorganism, or is a mammalian, plant or other cell culture.

Preferably, the host cell is *E. coli*.

According to a sixth aspect of the present invention there is provided allulose produced by a protein according to the first aspect of the invention.

According to a seventh aspect of the present invention there is provided a method of producing allulose comprising:
  i) providing a protein according to the first aspect of the invention; and
  ii) contacting the protein with a fructose substrate under conditions such that the fructose substrate is converted into allulose. A method of producing allulose is also provided by the invention, the method comprising contacting a protein according to the first aspect of the invention with a fructose substrate under conditions such that the fructose substrate is converted to allulose.

Advantageously, the protein is present in a host cell.

Alternatively, the protein is in isolated form.

Conveniently, the conditions comprise maintaining the protein and the fructose substrate at a temperature between 25° C. and 75° C., preferably between 50° C. and 60° C., more preferably between 52° C. and 55° C., more preferably 55° C.

Preferably, the conditions comprise maintaining the protein and the fructose substrate between pH 4 and pH10.

Advantageously, the conditions comprise maintaining the fructose substrate concentration between 75% and 95% (W/N).

According to an eighth aspect of the present invention there is provided a nucleic acid molecule comprising a polynucleotide sequence which:
  i) has at least 70% sequence identity to SEQ ID NO: 5, SEQ ID NO: 1 or SEQ ID NO: 3; or
  ii) hybridizes under highly stringent conditions to a polynucleotide having a sequence complementary to the sequence set forth in SEQ ID NO: 5, SEQ ID NO: 1 or SEQ ID NO: 3.

The nucleic acid molecule encodes a polypeptide having ketose 3-epimerase activity. The nucleic acid molecule may be in isolated form, according to one aspect of the invention.

According to a ninth aspect of the present invention there is provided a host cell comprising a recombinant nucleic acid molecule comprising a polynucleotide sequence encoding a polypeptide having ketose 3-epimerase activity, wherein the polynucleotide sequence:
  i) has at least 70% sequence identity to SEQ ID NO: 5, SEQ ID NO: 1 or SEQ ID NO: 3; or
  ii) hybridizes under highly stringent conditions to a polynucleotide having a sequence complementary to the sequence set forth in SEQ ID NO: 5, SEQ ID NO: 1 or SEQ ID NO: 3.

According to a tenth aspect of the present invention there is provided a vector comprising a nucleic acid molecule comprising a polynucleotide encoding a polypeptide having ketose 3-epimerase activity, wherein the polynucleotide sequence:
  i) has at least 70% sequence identity to SEQ ID NO: 5, SEQ ID NO: 1 or SEQ ID NO: 3; or
  ii) hybridizes under highly stringent conditions to a polynucleotide having a sequence complementary to the sequence set forth in SEQ ID NO: 5, SEQ ID NO: 1 or SEQ ID NO: 3.

According to an eleventh aspect of the present invention there is provided a method of producing allulose comprising the steps of:
  i) providing a vector comprising a nucleic acid molecule having a polynucleotide sequence encoding a protein having ketose 3-epimerase activity wherein the polynucleotide sequence: a) has at least 70% sequence identity to SEQ ID NO: 5, SEQ ID NO: 1 or SEQ ID NO: 3; or b) hybridizes under highly stringent conditions to a polynucleotide having a sequence complementary to the sequence set forth in SEQ ID NO: 5, SEQ ID NO: 1 or SEQ ID NO: 3;
  ii) synthesising the protein having ketose 3-epimerase activity encoded by the polynucleotide sequence;
  iii) contacting fructose with the protein having ketose 3-epimerase activity and maintaining the fructose and protein under conditions to permit the conversion of fructose to allulose; and
  iv) at least partially purifying the allulose produced in step iii).

The terms "polypeptide", "peptide" and "protein" are used interchangeably herein to refer to a polymer of amino acid residues. The terms also apply to amino acid polymers in which one or more amino acid residues is a modified residue, or a non-naturally occurring residue, such as an artificial chemical mimetic of a corresponding naturally occurring amino acid, as well as to naturally occurring amino acid polymers. The polypeptide may or may not be "isolated", that is to say removed from the components which exist around it when naturally occurring.

The term "amino acid" as used herein refers to naturally occurring and synthetic amino acids, as well as amino acid analogues and amino acid mimetics that have a function that is similar to naturally occurring amino acids. Naturally occurring amino acids are those encoded by the genetic code, as well as those modified after translation in cells (e.g. hydroxyproline, gamma-carboxyglutamate, and O-phosphoserine). The phrase "amino acid analogue" refers to compounds that have the same basic chemical structure (an alpha carbon bound to a hydrogen, a carboxy group, an amino group, and an R group) as a naturally occurring amino acid but have a modified R group or modified backbones (e.g. homoserine, norleucine, methionine sulfoxide, methionine methyl sulphonium). The phrase "amino acid mimetic" refers to chemical compounds that have different structures from, but similar functions to, naturally occurring amino acids. It is to be appreciated that, owing to the degeneracy of the genetic code, nucleic acid molecules encoding a particular polypeptide may have a range of polynucleotide sequences. For example, the codons GCA, GCC, GCG and GCT all encode the amino acid alanine.

The percentage "identity" between two sequences may be determined using the BLASTP algorithm version 2.2.2 (Altschul, Stephen F., Thomas L. Madden, Alejandro A Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389'-3402) using default parameters.

The term "ketose-3-epimerase activity" as used herein means that an enzyme is capable of catalyzing the inversion of stereochemistry of ketoses, in particular the conversion of fructose to allulose. For example, in one embodiment, "ketose-3-epimerase activity" is defined as being the capacity of an enzyme to increase the rate of interconversion of fructose to allulose by at least 10 micromol/min per mg of added enzyme (0.1 U/mg) over a reaction mixture under the same conditions in the absence of the enzyme. In alternative embodiments an increase in rate of interconversion of fructose to allulose of at least 0.05 U/mg or 0.2 U/mg is is considered to be "ketose-3-epimerase activity". A suitable assay for determining the activity of an enzyme in converting D-fructose into allulose is as follows. A reaction mixture comprising 1 ml D-fructose (50 g/L), Tris-HCL buffer (50 mM, pH 8.0), and 0.5 µM enzyme is incubated at 55° C. for 2 minutes.

The reaction is stopped after 10 minutes by boiling. The amount of D-allulose produced is determined by the HPLC method. One unit of enzyme activity is defined as the amount of enzyme catalysing the formation of 1 µmol of D-allulose/min at pH 8.0 and 55° C. (J. Agric. Food Chem. 2011, 59, 7785-7792).

The terms "gene", "polynucleotides", and "nucleic acid molecules" are used interchangeably herein to refer to a polymer of multiple nucleotides. The nucleic acid molecules may comprise naturally occurring nucleic acids (i.e. DNA or RNA) or may comprise artificial nucleic acids such as peptide nucleic acids, morpholin and locked nucleic acids as well as glycol nucleic acids and threose nucleic acids.

The term "nucleotide" as used herein refers to naturally occurring nucleotides and synthetic nucleotide analogues that are recognised by cellular enzymes.

The term "vector" as used herein refers to any natural or artificial construct containing a nucleic acid molecule in which the nucleic acid molecule can be subject to cellular transcription and/or translation enzymes. Exemplary vectors include: a plasmid, a virus (including bacteriophage), a cosmid, an artificial chromosome or a transposable element.

The term "host cell" as used herein refers to any biological cell which can be cultured in medium and used for the expression of a recombinant gene. Such host cells may be eukaryotic or prokaryotic and may be a microorganism such as a bacterial cell, or may be a cell from a cell line (such as an immortal mammalian cell line).

The term "highly stringent conditions" as used herein when referring to hybridization conditions means: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C. It is known in the art that hybridization techniques using a known nucleic acid as a probe under highly stringent conditions, such as those set forth in the specification, will identify structurally similar nucleic acids.

The term "allulose" as used herein refers to a monosaccharide sugar of the structure shown in Formula I. It is also known as "D-Psicose".

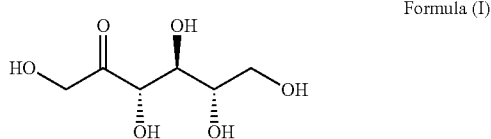 [SMILES: O=C(CO)[C@@H](O)[C@@H](O)[C@@H](O)CO]

Formula (I)

The term "fructose" as used herein refers to a monosaccharide sugar having the structure shown in Formula II. Examples of fructose substrate include but are not limited to crystalline fructose and crystalline fructose greens. As used herein, "crystalline fructose greens" refers to a process stream created during fructose crystallization from the non-crystallizing portion of the crystallization mother liquor.

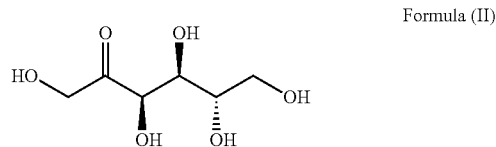 [SMILES: O=C(CO)[C@H](O)[C@@H](O)[C@@H](O)CO]

Formula (II)

The term "recombinant" as used herein refers to a nucleic acid molecule or a polypeptide which is located in a non-naturally occurring context and which has been produced by artificial intervention. For example, a first polypeptide isolated from other polypeptides or linked by a peptide bond to a second polypeptide sequence having a different amino acid sequence from any polypeptide with which the first polypeptide is associated in nature is a recombinant polypeptide.

BRIEF DESCRIPTION OF THE FIGURES

FIG. 1 shows the amino acid sequence of the ketose-3-epimerase from *Clostridium scindens* in accordance with one embodiment of the present invention (SEQ ID NO: 2).

FIG. 2 shows the amino acid sequence of the ketose-3-epimerase from *Clostridium hylemonae* in accordance with another embodiment of the present invention (SEQ ID NO: 4).

FIG. 3 shows the amino acid sequence of the ketose-3-epimerase from *Desmospora* sp. in accordance with a further embodiment of the present invention (SEQ ID NO: 6).

FIG. 4 shows the amino acid sequence of a previously known xylose isomerase from *Clostridium cellulolyticum* (SEQ ID NO: 8).

FIG. 5 shows a sequence comparison between the three ketose-3-epimerases shown in FIGS. 1 to 3 and three previously known ketose-3-epimerases. Completely conserved residues are highlighted.

FIG. 7 shows the optimised gene sequence (SEQ ID NO: 7) encoding the amino acid sequence shown in FIG. 4 and a comparison of the optimised sequence with the original sequence.

FIG. 8 shows the optimised gene sequence (SEQ ID NO: 5) encoding the amino acid sequence shown in FIG. 3, and a comparison of the optimised sequence with the original sequence.

FIG. 9 shows the optimised gene sequence (SEQ ID NO: 1) encoding the amino acid sequence shown in FIG. 1, and a comparison of the optimised sequence with the original sequence.

FIG. 10 shows the optimised gene sequence (SEQ ID NO: 3) encoding the amino acid sequence shown in FIG. 2, and a comparison of the optimised sequence with the original sequence.

FIG. 15 shows the amino acid sequence of an artificial variant of the naturally occurring ketose-3-epimerase from *Desmospora* sp. (SEQ ID NO. 13).

BRIEF DESCRIPTION OF THE SEQUENCE LISTING

Figure 6:
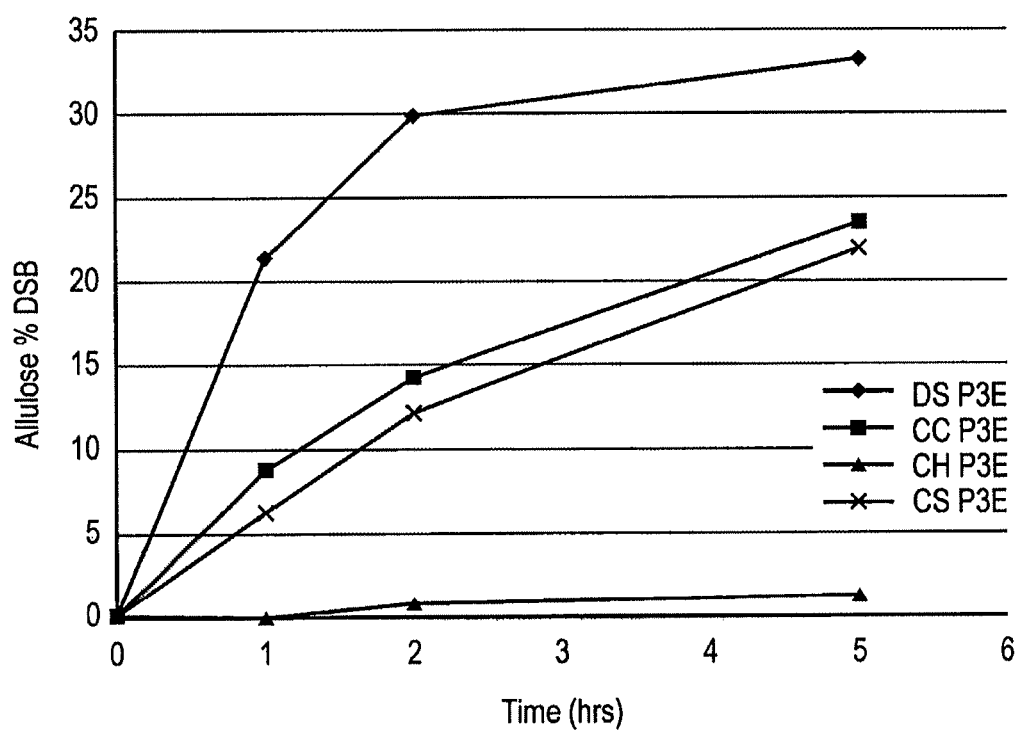
FIG. 6 is a graph showing the rate of conversion of fructose to allulose by *E. coli* transformed to express an enzyme in accordance with an embodiment of the present invention and a control.

SEQ ID NO: 1 shows a gene sequence (optimised for expression in *E. coli*) encoding a ketose-3-epimerase from *Clostridium scindens*.

SEQ ID NO: 2 shows the amino acid sequence of the ketose-3-epimerase encoded by the gene sequence of SEQ ID NO. 1.

SEQ ID NO: 3 shows a gene sequence (optimised for expression in *E. coli*) encoding a ketose-3-epimerase from *Clostridium hylemonae*.

SEQ ID NO: 4 shows the amino acid sequence of the ketose-3-epimerase encoded by the gene sequence of SEQ ID NO. 3.

SEQ ID NO: 5 shows a gene sequence (optimised for expression in *E. coli*) encoding a ketose-3-epimerase from *Desmospora* sp. 8437.

SEQ ID NO: 6 shows the amino acid sequence of the ketose-3-epimerase encoded by the gene sequence of SEQ ID NO. 5.

SEQ ID NO: 7 shows a gene sequence (optimised for expression in *E. coli*) encoding a ketose-3-epimerase from *Clostridium cellulolyticum*.

SEQ ID NO: 8 shows the amino acid sequence of the ketose-3-epimerase encoded by the gene sequence of SEQ ID NO. 7.

SEQ ID NO: 9 shows the naturally occurring gene sequence encoding the ketose-3-epimerase from *Clostridium scindens*.

SEQ ID NO: 10 shows the naturally occurring gene sequence encoding the ketose-3-epimerase from *Clostridium hylemonae*.

SEQ ID NO: 11 shows the naturally occurring gene sequence encoding the ketose-3-epimerase from *Desmospora* sp. 8437.

SEQ ID NO: 12 shows the naturally occurring gene sequence encoding the ketose-3-epimerase from *Clostridium cellulolyticum*.

SEQ ID NO: 13 shows the amino acid sequence of an artificial variant of the ketose-3-epimerase of *Desmospora* sp. 8437.

DETAILED DESCRIPTION

The present invention relates, in general terms, to a protein comprising a polypeptide having an amino acid sequence shown in one of SEQ. ID NO. 2, 4 or 6. The source organisms of the polypeptides of SEQ. ID NOS. 2, 4 and 6 are shown in Table 1.

TABLE 1

| Source Organism | SEQ. ID NO. |
|---|---|
| *Clostridium scindens* ATCC ® 35704 | 2 |
| *Clostridium hylemonae* DSM 15053 | 4 |
| *Oesmospora* sp.8437 | 6 |

However, in alternative embodiments, the polypeptide sequence is not identical to that shown in SEQ. ID NOs. 2, 4 or 6 but has at least 70% sequence identity thereto. It is preferred that the polypeptide sequence has at least 80%, 90%, 95% or 99% sequence identity, or 100% sequence identity, to SEQ. ID NO. 2, 4 or 6.

For example, in one embodiment the polypeptide sequence comprises the sequence of SEQ. ID NO. 13 which has 89% sequence identity to SEQ. ID NO. 6. The polypeptide sequence has ketose 3-epimerase activity.

Thus in some embodiments, one or more amino acids of the peptides are omitted or are substituted for a different amino acid, preferably a similar amino acid. A similar amino acid is one which has a side chain moiety with related properties and the naturally occurring amino acids may be categorized into the following groups. The group having basic side chains: lysine, arginine, histidine. The group having acidic side chains: aspartic acid and glutamic acid. The group having uncharged polar side chains: aspargine, glutamine, serine, threonine and tyrosine. The group having non-polar side chains: glycine, alanine, valine, leucine, isoleucine, proline, phenylalanine, methionine, tryptophan and cysteine. Therefore it is preferred to substitute amino acids within these groups.

It is generally preferred that the polypeptide conforms with the chemistry of naturally occurring polypeptides (although it may be synthesized in vitro) but in some alternative embodiments the polypeptide is a peptidomimetic, that is to say a modification of a polypeptide in a manner that will not naturally occur. Such peptidomimetics include the replacement of naturally occurring amino acids with synthetic amino acids and/or a modification of the polypeptide backbone. For example in some embodiments, the peptide bonds are replaced with a reverse peptide bond to generate a retro-inverso peptidomimetic (see Méziére et al J Immunol. 1997 Oct. 1; 159(7):3230-7, which is incorporated herein by reference.) Alternatively, the amino acids are linked by a covalent bond other than a peptide bond but which maintains the spacing and orientation of the amino acid residues forming the polymer chain.

All such modified and unmodified polypeptides of the invention have ketose-3-epimerase polymerase activity. That is to say, the protein, when purified or expressed in a host cell, has the capacity to catalyze the conversion of fructose to allulose. Suitable conditions for testing the presence of ketose-3-epimerase activity are shown in Example 1.

The polypeptide of the invention may be contained within a whole cell or may be an isolated protein, a partially purified protein or an immobilized protein. Purification of the protein may be by standard methods such as cell disruption and filtration. Other standard methods are known to those skilled in the art.

In embodiments of the present invention, there is provided a nucleic acid molecule which comprises a polynucleotide sequence encoding a protein having an amino acid sequence with at least 70% sequence identity to SEQ. ID NO. 2, 4 or 6, where the protein has ketose-3-epimerase activity. For example, in one embodiment the nucleic acid molecule comprises a sequence encoding the polypeptide sequence of SEQ. IN NO. 13.

In addition to the sequence specifically encoding the protein of the invention, the nucleic acid molecule may contain other sequences such as primer sites, transcription factor binding sites, vector insertion sites and sequences which resist nucleolytic degradation (e.g. polyadenosine tails). The nucleic acid molecule may be DNA or RNA and may include synthetic nucleotides, provided that the polynucleotide is still capable of being translated in order to synthesize a protein of the invention.

As described above, the amino acid sequence of the protein of the present invention may differ from the specific sequences disclosed herein. In preferred embodiments, the nucleic acid molecule comprises a polynucleotide having the sequence of SEQ. ID NO. 1, 3 or 5, which has been optimised by expression in $E.\ coli$ host cells. In alternative embodiments, the polynucleotide sequence has at least 70% sequence identity to any one of SEQ. ID NO. 1, 3 or 5 and encodes a protein which has ketose-3-epimerase activity. It is preferred that the polynucleotide sequence has at least 80%, 90%, 95% or 99% sequence identity, or 100% sequence identity, to one of SEQ. ID NO. 1, 3 or 5. In alternative embodiments the nucleic acid molecule comprises a polynucleotide sequence which hybridizes under highly stringent conditions to a polynucleotide having a sequence complementary to the sequence set forth in SEQ ID NO: 1, 3 or 5 and which encodes a protein which has ketose-3-epimerase activity. In some embodiments, there is provided a nucleic acid molecule comprising a polynucleotide having the sequence of SEQ. ID NO. 9, 10 or 11, which are the naturally occurring sequences of the enzymes.

In some embodiments, the nucleic acid molecule forms part of a vector such as a plasmid. In addition to the nucleic acid sequence described above, the plasmid comprises other elements such as a prokaryotic origin of replication (for example, the $E.\ coli$ OR1 origin of replication) an autonomous replication sequence, a centromere sequence; a promoter sequence, upstream of the nucleic acid sequence, a terminator sequence located downstream of the nucleic acid sequence, an antibiotic resistance gene and/or a secretion signal sequence. A vector comprising an autonomous replication sequence is also a yeast artificial chromosome.

In some alternative embodiments, the vector is a virus, such as a bacteriophage and comprises, in addition to the nucleic acid sequence of the invention, nucleic acid sequences for replication of the bacteriophage, such as structural proteins, promoters, transcription activators and the like.

The nucleic acid molecule of the invention may be used to transfect or transform host cells in order to synthesize the protein of the invention. Suitable host cells include prokaryotic cells such as $E.\ coli$ and eukaryotic cells such as yeast cells, or mammalian or plant cell lines. Host cells are transfected or transformed using techniques known in the art such as electroporation; calcium phosphate base methods; a biolistic technique or by use of a viral vector.

After transfection, the nucleic acid molecule of the invention is transcribed as necessary and translated. In some embodiments, the synthesized protein is allowed to remain in the host cell and cultures of the recombinant host cell are subsequently used. In other embodiments, the synthesized protein is extracted from the host cell, either by virtue of its being secreted from the cell due to, for example, the presence of secretion signal in the vector, or by lysis of the host cell and purification of the protein therefrom.

The protein of the present invention is used to catalyze the conversion of fructose to allulose. In some embodiments, the protein is present in host cells and is mixed, to form a conversion mixture, with a fructose substrate, such as borate buffered fructose substrate, at a concentration from 1 to 1000 g/L under suitable conditions, such as incubation at a temperature from 25° C. to 75° C., pH from 4 to 10. The conversion mixture may also comprise a solvent and optionally additional co-solvents (in addition to water) for example ethanol, toluene and methanol. The fructose substrate may also contain other sugars such as glucose or sucrose. The protein catalyzes a conversion of the fructose substrate to allulose. In practice, not all fructose in the conversion mixture is converted to allulose so there is typically a subsequent step of extracting and purifying the allulose through evaporation and crystallisation. Residual fructose in the mixture may be removed by yeast fermentation.

In alternative embodiments, the protein of the present invention is provided in purified form and mixed with a fructose substrate together with suitable solvent for an entirely in vitro conversion. In one embodiment the conditions are pH 4-10, a temperature between 30° C. and 70° C. and a fructose concentration of 10-95% w/v, with water as the solvent. Alternative concentration ranges for fructose include but are not limited to 20-95%, 30-95%, 40-95%, 50-95%, 60-95%, 70-95%, 75-95%. It is particularly preferred that the fructose substrate is provided at a concentration between 70 and 95%. In other preferred embodiments, the fructose concentration is 75-95%.

The conversion reaction of ketoses is usually carried out using a substrate concentration of 1-60% (w/v), preferably about 5-50%. It is a particular advantage of the present invention that the protein can be used in ketose conversion reactions under usual operating conditions but with higher fructose concentrations than have previously been used. Thus, a greater volumetric productivity is possible with the protein of the present invention.

In some embodiments, the protein of the present invention is immobilised on a solid substrate. This provides the advantage that the enzyme has a longer usage life, can be packed in a smaller fixed bed reactor, and has greater tolerance to contaminants and to fluctuations in the conditions of the process. Exemplary solid substrates include ion exchange resins and polymer encapsulations. In some embodiments, the protein of the present invention is immobilised on Duolite A568 resin. In some embodiments, the protein of the invention is immobilised on a substrate by weakly basic ion exchange (i.e. electrostatic interaction based on the charge of the protein and the charge of a substrate such as a resin). In other embodiments the protein is immobilised by non-specific binding to porous regions of a substrate such as a resin.

In another embodiment the invention relates to a method of producing allulose. The method comprises the following steps.

1) Providing a vector comprising a nucleic acid molecule having at least 70% sequence identity to SEQ ID NO:1, SEQ ID NO:3 or SEQ ID NO: 5.
2) Transforming competent host cells with said vector.
3) Optionally, culturing the transformed host cells.
4) Mixing the transformed cells with a fructose substrate and maintaining under conditions to permit conversion of fructose to allulose.
5) Purifying the allulose produced using standard methods in the art, such as evaporation and crystallization.

In alternative embodiments, step 4) is omitted. Instead, the protein encoded by said nucleic acid molecule is isolated from the transformed host cell and optionally immobilized on a substrate. The protein is then mixed with the fructose substrate and maintained under conditions to permit conversion of fructose to allulose. Step 5) is then performed. In other embodiments, step 2) is omitted and the protein is instead synthesised by in vitro translation. Subsequently, the protein is isolated and mixed with the fructose substrate.

Allulose produced by the method of the present invention may be used in a product for human and/or animal consumption. In some embodiments, the product may be a food product, a beverage product, a pharmaceutical product, a nutritional product, a sports product, or a cosmetic product.

For example, when the product is a food product, the food product can be selected from the group consisting of a confectionary product, a dessert product, a cereal product, baked goods, frozen dairy products, meats, dairy products, condiments, snack bars, soups, dressings, mixes, prepared foods, baby foods, diet preparations, syrups, food coatings, dried fruit, sauces, gravies, and jams/jellies. In some embodiments, the food product may comprise allulose produced by the method of the present invention as a coating or frosting formed on the surface of the product.

Alternatively, when the product is a beverage product, the beverage product can be selected from the group consisting of a carbonated beverage, a non-carbonated beverage, fruit-flavoured beverage, fruit-juice, tea, milk, coffee, and the like.

EXAMPLES

Example 1

In this example, host cells were transformed to express one of three putative ketose-3-epimerase enzymes. Transformed host cells were tested for ketose-3-epimerase activity by incubating them with a fructose substrate.

Materials
Borate Buffer 1M pH8:
i) 62 g boric acid dissolved in 1l DI water
ii) adjust to pH8 with 10M NaOH
iii) store in 1 L bottle in 4° C. refrigerator
Borate Buffered Fructose Substrate:
i) 970 g liquid fructose (77% DS) in 50 ml Borate buffer pH8
ii) water up to 1 L final volume
iii) adjust pH to 8 with 5M NaOH
Expression Medium LB—4×2.8 L baffled shake flasks:
i) 10 g tryptone, 7 g NaCl and 10 g yeast in 1 L DI water
ii) autoclave
Methods Three putative ketose-3-epimerase gene sequences and one control sequence were selected to be synthetically constructed by Genscript USA, Inc. The putative ketose-3-epimerase sequences encoded:

i) hypothetical protein CLOSCI_02526 from *Clostridium scindens* ATCC® 35704 (accession ZP_02432281) (SEQ. ID NO. 2)
ii) hypothetical protein CLOHYLEM_05645 from *Clostridium hylemonae* DSM 15053 (accession ZP_03778576.1) (SEQ. ID NO. 4)
iii) D-tagatose 3-epimerase from *Desmospora* sp. 8437 (accession ZP_08466075) (SEQ. ID NO. 6).

The control sequence encoded a xylose isomerase protein from *Clostridium cellulolyticum* H10 (accession YP_002505284) (SEQ. ID NO. 8).

The genes were synthetically constructed with sequences optimized for expression in *E. coli* (see FIGS. 7 to 10) and each of the resulting four genes was cloned into an expression vector, pET15b. Other combinations of microorganisms and expression vectors known to one skilled in the art are expected to perform equally well.

Competent cells used for the transformation were prepared by inoculating 3 ml Lysogeny Broth (LB) with *E. coli* BL21 (DE3) and allowing the bacteria to propagate overnight at 37° C. 300 ml LB was inoculated with this 3 ml culture and the cells were grown at 37° C. with shaking to 0.7-1.0 OD (600).

Optical densities (OD) were measured in a 1 cm cell at 600 nm wavelength on a typical spectrophotometer. The cells were chilled on ice for 10 mins and then spun down at 7500×g at 4° C. for 15 minutes. The media was poured off and the cells resuspended in 300 ml cold water. The spin was repeated and the cell resuspended in 150 ml cold water. The spin was repeated again and the cells were suspended in about 2 ml cold sterile 10% glycerol. The cells were spun down as previously and were suspended in about 2 ml cold sterile 10% glycerol. The suspension was divided into 100 µl aliquots in sterile eppendorf tubes and stored at −80° C.

The expression vectors provided by Genscript were subsequently used to transform competent *E. coli* BL21 (DE3) by electroporation and positive transformants were selected on ampicillin containing LB agar. 1 L LB was poured into each of four 2.8 L baffled flasks and was autoclaved. Once cool, 1 ml of 100 mg/l ampicillin was added to each flask aseptically and each flask was inoculated with 2-3 ml of the overnight culture of competent cells prepared above (1 flask per expression strain). The cells were allowed to grow for about 3 hours at 37° C. with 200 rpm shaking in order to achieve an OD of 0.8-1.5. 1 ml of a freshly prepared 1M isopropyl β-D-1-thiogalactopyranoside solution was added to each flask, the temperature was reduced to room temperature (i.e. 25-30° C.) and induction was allowed to proceed for about 5 hours. The cells were spun down at about 5000×g for 30 minutes at 4° C. and the supernatant decanted. The cell pellet was transferred to a weighed 50 ml centrifuge tube and the cell mass was recorded. The cells were resuspended in a few ml of sterile glycerol (10% w/w) and were frozen at −80° C.

The conversion activity of the cells was checked by mixing the whole cells into a borate buffered fructose substrate and analysing by HPLC using DP 1-4 method with a $Ca^{2+}$ column. Four flasks containing 250 ml of borate buffered fructose substrate were warmed to 55° C. and the frozen cells were thawed at room temperature. The cells were pelleted at 6500×g and resuspended in DI water. 2 g (wet weight) of cells were mixed in borate buffered fructose substrate and were incubated at 55° C. with 90 rpm mixing in a 1 L baffled flask. Samples were taken at 0, 1, 2 and 5 hours, and were submitted for HPLC analysis.

HPLC analysis consisted of injection of 20 µL of a sample to be analysed at 0.1% (W/N) into a chromatographic system consisting of a water mobile phase with a flow rate between 0.1 and 1.5 mL/min and a stationary phase consisting of a resin of particle size between 1 and 10 µm in the $Ca^{2+}$ form maintained at 80° C. Peaks were detected and quantitated by a refractive index detector and qualitatively assigned based on retention time of known standards.

Results and Discussion

Three protein sequences were identified to be tested as ketose-3-epimerase proteins. The sequences of these proteins are given in FIGS. 1 to 3 (SEQ. ID NOS 2, 4 and 6). The xylose isomerase from *Clostridium cellulolyticum* H10, used as a control, has previously been suggested to produce allulose from fructose. Its amino acid sequence is shown in FIG. 4 (SEQ. ID NO. 8).

The amino acid sequences of these proteins were aligned with those of other known ketose-3-epimerases and the aligned sequences are shown in FIG. 5. Completely conserved residues are highlighted. There are very few conserved residues between these sequences, with fewer than 65% of the residues being conserved from one sequence to the next.

The degree of sequence identity between each of the sequences of SEQ. ID NOS. 2, 4, and 6 with each of Accession Nos NP_535228 and BAA24429 and SEQ. ID NO 8 was determined. The results are shown in Table 2. Between 40 and 63% sequence identity for the known ketose-3-epimerases was observed for each of the selected protein sequences. There was no overall strong homology based on the sequence alignment of all of the sequences. The selected proteins had genes optimized for expression by *E. coli* synthetically constructed and cloned into commercial expression vector pET15b by Genscript. Transformation of *E. coli* BL21 (DE3) was successful for each construct and frozen stocks of each strain were saved along with the expression vectors. Protein expression was carried out on the 1 L scale and whole cells were harvested as the crude catalyst. Conversion activity was checked and FIG. 6 shows the % DSB allulose produced during the experiment by the four different strains tested.

TABLE 2

| Organism | SEQ ID NO. | % Identical Protein Sequence | | |
|---|---|---|---|---|
| | | *A. tumefaciens* (accession NP_535228) | *P. cichorii* (accession BAA24429) | *C. cellulolyticum* (accession NC_011898) |
| *C. scindens* | 2 | 59 | 43 | 43 |
| *C. hylemonae* | 4 | 60 | 41 | 63 |
| *Desmospora* sp. | 6 | 50 | 43 | 51 |

Expression of the three putative ketose-3-epimerases was successfully carried out and all three could successfully convert fructose into allulose, confirming that each protein is, indeed, a ketose-3-epimerase.

The most active protein was DS P3E (D-tagatose 3-epimerase from *Desmospora* sp. 8437, SEQ. ID NO. 6) which was capable of converting 30% of a 750 g/L fructose solution in just 2 hours utilizing 8 g of wet cell weight per litre for a volumetric productivity of 112 g/L/hour.

Example 2

In this example, the current best conditions for cell growth and conversion were carried out on an 18 L scale to determine scaleability and to produce allulose for further sensory and clinical investigation. Following the conversion, an initial clean-up step to remove fructose was carried out. This example was for the purpose of identifying the scaleability of this process, any unforeseen problems with scale-up and the amount of allulose that could reasonably be produced in a laboratory.

Materials
Isopropylthiogalactopyranoside (IPTG)
Filter sterilized aqueous ampicillin solution 100 mg/ml
Crystalline fructose greens
Liquid fructose (77% DS)

Growth media:
i) 25 g NaCl, 25 g Staleydex® 333, 6 g glycerol, 50 g tryptone (Difco), 60 g yeast extract (Difco), 8 g potassium phosphate dibasic and 8 g potassium phosphate monobasic in 61 DI water
ii) adjust pH to ~7.8 with Tris base (solid)
iii) autoclave 1 L per flask in 6×2.8 L baffled flasks with foil on top Tris buffer 1M pH8:
iv) 121 g in 1 L DI water
iv) adjust pH to 8 with HCl
iv) store in 1 L bottle in 4° C. refrigerator Method
To propagate the cells, six overnight cultures of 5 ml LB medium supplemented with 100 µg/ml ampicillin were started. The cultures were inoculated with the *E. coli* production strain (BL21-DE3 pET15b-DS-P3E expressing the protein of SEQ. ID NO. 6) and allowed to grow overnight (~16 hours) at 37° C. 6 L of growth media was prepared and autoclaved as described above, 5 ml of the overnight culture was added to each flask and this was shaken at 190 rpm at 37° C. for 4 hours. 1 mM IPTG was added to each flask by preparing a fresh 1M solution and adding 1 ml per litre to the flasks. The temperature was reduced to 25° C. with continued shaking for 14-16 hours.

In order to harvest the cells, the cultures were centrifuged at 6000 rpm for 20 minutes using floor centrifuge in Mod 322 and 1 L bottles (filled with not more than 800 ml of media). The media was decanted into a kill bucket, to which 1% by volume bleach was added, and was allowed to sit for 30 minutes. The centrifuge tubes were weighed and 3 ml DI water per gram of cells was added to the tubes. The cells were re-suspended using a spatula and vortex genie until a uniform cell slurry was obtained. The suspension was transferred to 40 ml centrifuge tubes and re-pelleted at 6500×g. The wash was decanted into the kill bucket and the cells were re-suspended in the same volume of water.

The propagation and harvesting of cells was repeated with a second batch of cells.

The crystalline fructose greens conversion substrate was prepared by warming a 5 gallon (18.9 L) bucket of crystalline fructose greens to room temperature and adding 16,506 g crystalline fructose greens to a sanitised 5 gallon (18.9 L) plastic bucket with an 18 L calibration mark. 900 ml of 1M Tris pH 8.0 prepared as above was added to the bucket, followed by water up to the 18 L calibration mark, and was mixed using an overhead mixer until homogeneous. The mixture and the unused crystalline fructose greens were returned to a cold room for storage.

The liquid fructose conversion substrate was prepared by combining 17,460 g liquid fructose (77% DS) and 500 ml of 1M Tris pH 8.0 (prepared as above) in a sanitised 5 gallon (18.9 L) plastic bucket with an 18 L calibration mark. Water was added up to 18 L calibration mark and an overhead mixer was used to mix until homogeneous.

For the whole cell conversion, 18 L of prepared crystalline fructose greens conversion substrate was heated to 55° C. in a water bath and was gently mixed with an overhead mixer at about 150 rpm. The re-suspended cell paste obtained from the cell harvesting was added to a total of 100 g wet weight of cells. After 5 hours a sample was removed and was submitted HPLC analysis. The reaction was stopped by refrigerating the entire bucket at 4° C. A sample was submitted for microbial analysis for *E. coli*, coliforms and TPC.

The whole cell conversion process was repeated with 18 L of prepared liquid fructose conversion substrate. 120 g of cells wet weight was used and samples were taken at 2 and 4 hours for HPLC Analysis.

Yeast fermentation was used to remove fructose from the crystalline fructose greens conversion substrate. The crystalline fructose greens conversion product was diluted with 2 volumes of water for a final concentration of ~250 g/L of combined allulose and fructose in a total volume of 54 L. The 54 L of diluted mixture was split between four sanitised 5 gallon (18.9 L) buckets, with approximately 13 L per bucket. Two of the buckets were stored in a refrigerator. The remaining two buckets were set up with vigorous agitation from overhead mixers and aeration from 9 L/min air pumps with diffusers for approximately 0.3 VVM air flow. 120 g dry active baker's yeast (Fleishman's brand) was added to each bucket, and these were mixed and aerated for 2 days (~36 hours) with occasional sampling for DP1-4 allulose analysis. The buckets were transferred to the cold room overnight to allow the yeast to settle. The supernatant was then transferred to two new clean sanitised buckets and the remaining yeast fraction was transferred to the two refrigerated crystalline fructose greens-containing buckets prepared above. The agitation and mixing process was repeated, followed by the removal of yeast. Following the yeast fermentation step, about 45 L of supernatant was obtained and sterile filtered into 3 clean sanitised buckets, which were stored at 4° C. for further processing.

Results and Discussion

Approximately 220 g of BL21 (DE3) pET-15b-DS P3E cells were obtained from 12 L of culture and split into two 18 L bioconversions as described above. Thus, the total whole cell biocatalyst concentration was 5.6 g/L for the crystalline fructose greens conversion and 6.7 g/L for the liquid fructose conversion.

Figure 11:
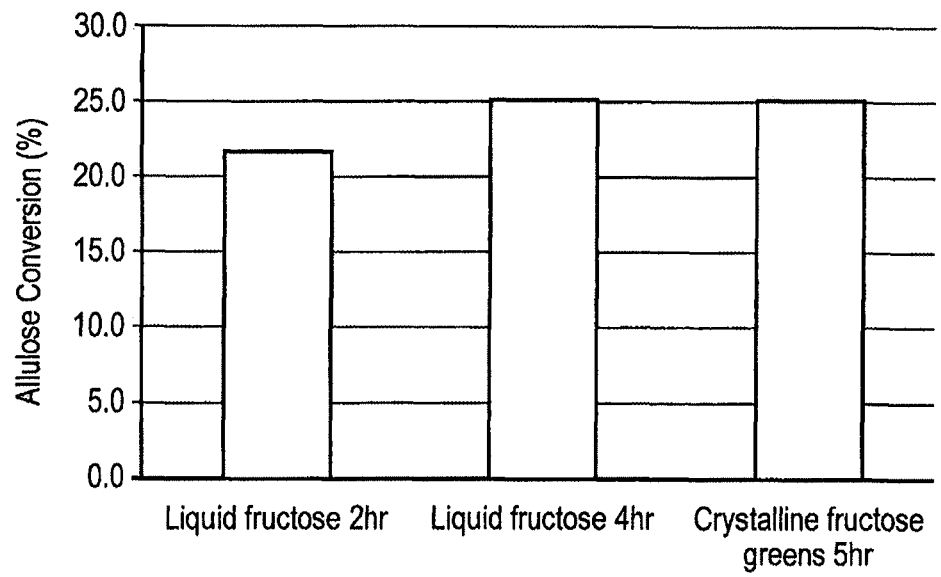
FIG. 11 is a graph showing the preparation of conversion of fructose substrate to allulose by *E. coli* transformed to express an enzyme in accordance with one embodiment of the present invention (the ketose-3-epimerase from *Desmospora* sp) at 18 L scale.

FIG. 11 shows that both conversions rapidly reached ~25%, calculated as allulose as a percentage of allulose+ fructose. This is slightly lower but very near the conversion level previously achieved using this cell type and similar conversion media on the small scale. Conversion had already reached 22% after just 2 hours with the liquid fructose substrate.

In each 18 L conversion, approximately 3.3 kg of allulose was produced. There did not appear to be a significant difference between the two substrates.

The scale up from 250 ml did not produce any unforeseen issues and proceeded as expected.

The microbial testing resulted in no live *E. coli* with a negative result and <3 coliforms per gram, and a total plate count of two. Therefore, a temperature of 55° C. combined with a high percentage of DS syrup was sufficient to kill the whole cell biocatalyst.

The bioconversion of fructose to allulose using the newly identified enzyme DS P3E was successfully scaled up to 18 L.

Example 3

An *E. coli* strain containing the newly identified DS P3E protein (SEQ ID NO: 6) was produced by two 10 L fermentations in a fermentation lab using a pH control feed batch culture method with glucose yeast extract media. The fermentations proceeded as expected.

During the fermentation batch growth and fed batch phases the cells grew exponentially with a doubling time of approximately 1 hr. Glucose concentration dropped from about 9 g/L to <1 g/L in about 5.5 hours (OD~28). During the Induction phase for enzyme production, the OD continued to rise to about 130 and then was not observed to change significantly. Harvesting of the fermentation by centrifugation resulted in 4.5 kg (10 lbs) of wet cell paste or approximately 1.1 kg (2.5 lbs) dry cell weight.

Fructose substrate (836 kg DS (dry solids) basis) was diluted to 69% DS (920 grams/L) with RO water and heated to 52° C. and pH adjusted to 7.8. Low agitation (~50 rpms) was utilized to promote mixing throughout the reaction and the entire batch of 4.5 kg (wet paste) of expressed whole cells from above was added to the reaction and a time 0 sample was taken. This provided a 0.48 g/L biocatalyst load which is similar to the previously tested lab scale conversions, however, the substrate concentration was higher at 920 g/L. Samples were taken at 4 and 16 hrs and analyzed by HPLC.

No loss of DS was observed and no bioproducts were produced during the reaction. The reaction proceeded nearly to the equilibrium value of ~30% allulose at the end of the 16 hr reaction. At 4 hrs the reaction had already proceeded to 18% conversion. The volumetric conversion rate previously obtained using 0.5 g/L biocatalyst with 750 g/L substrate (Examples 1 and 2) was 46 g/L*hr or per unit biocatalyst 92 g/L*hr/gram biocatalyst. Here, using a higher substrate concentration and slightly lower temperature (52° C. vs 55° C.), the volumetric conversion rate was 41 g/L*hr or 85 g/L*hr/gram biocatalyst (calculated using 4 hr data point). This demonstrates the remarkable flexibility of the epimerase reaction. When the reaction was completed at 16 hrs, 230 kg of allulose were present in the 28:72 mixture of allulose:fructose.

Example 4

Figure 12:
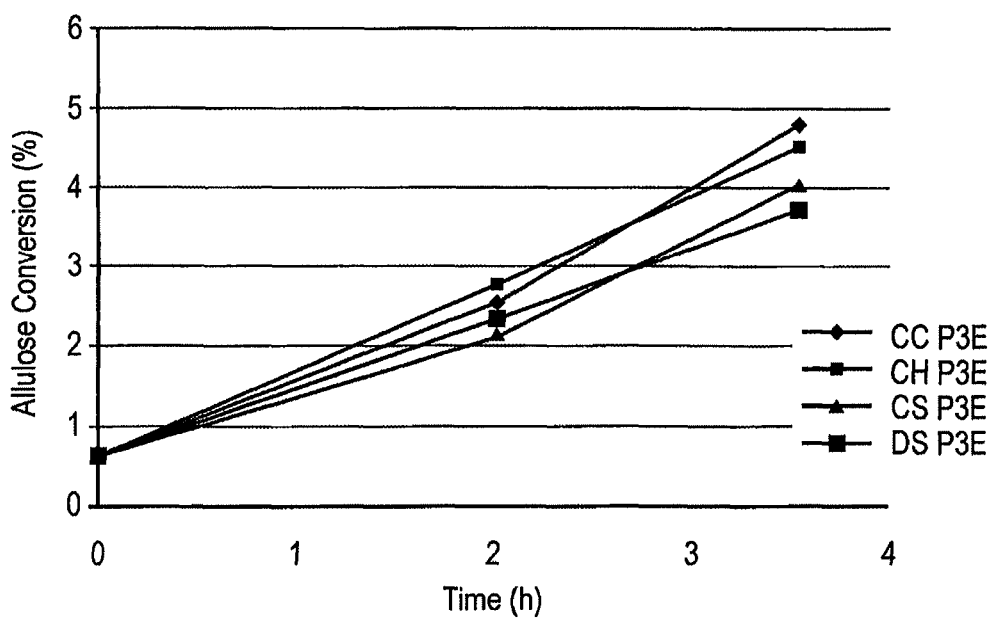
FIG. 12 is a graph showing the rate of allulose conversion by enzymes according to embodiments of the invention (CH P3E, CS P3E and DS P3E) and a known ketose-3-epimerase (CC P3E).

Conversion of fructose by the four different enzymes (SEQ ID No 2, 4, 6 and 8) was compared on Tris buffered fructose substrate at 750 g/L. Cells were induced at 16° C. instead of 25-30° C. and the rate of conversion was slower than in previous experiments. To 200 mL of the substrate, 2 g wet weight of resuspended cells was added in 500 mL baffled flasks and incubated at 55° C. with 90 rpm shaking. Samples were taken at 2 hrs and 3.5 hrs for HPLC analysis. The results are shown in FIG. 12 in which CC P3E corresponds to SEQ ID NO. 8 and CH P3E, CS P3E and DS P3E correspond to SEQ ID NOs. 4, 2 and 6, respectively. In this experiment, all 4 strains expressing one of the proteins set forth in SEQ ID 2, 4, 6 or 8 appear to have approximately the same level of activity converting approximately 5% of the substrate to allulose in 3.5 hrs.

Example 5

In this example, the first trial of allulose production using immobilised enzymes was carried out. This example was for the purpose of improving enzyme utilisation.

Materials

Lyophilized enzyme powder as prepared from Codexis, Lot D13007 or D13008

*Desmospora* sp. Psicose 3-epimerase

Duolite A568 (Dow)

Amberlite XAD2 (Sigma)

Tris buffer 1M:
i) Prepared in water by dissolving at a concentration of 1M
ii) Adjusted pH to 8.0 with HCl
iii) Diluted to 100 mM before use Crystalline Fructose Greens, 80% dry solids with a composition of:
i) 90% DSB fructose
ii) 7% DSB dextrose iii) 3% DP2+
iv) Other monosaccherides
MnCl$_2$ (Sigma)
Method
1) Small Scale Immobilisation In order to test efficiency of immobilisation, a small fixed bed reaction was carried out in jacketed columns of approximately 30 ml volume (11 mm×300 mm column dimensions). Both XAD2 and A568 resin was washed several times with water to remove fines (i.e. fine resin particles (i.e. broken/fractured particles) that are a by-product of resin manufacturing) and any residuals from manufacturing. 2 g of lyophilised enzyme (i.e. epimerase) was dissolved in approximately 50 ml of water and split into two aliquots. The pH was measured and determined to be 6.5. Approximately 30 ml of each resin was incubated with one aliquot of epimerase solution for approximately one hour at room temperature and light agitation. The resins were then packed into the jacketed column and peristaltic pumps were used to recycle the epimerase solution through the fixed bed for an additional two hours. The columns were then washed with 10 bed volumes of Tris buffer 100 mM pH 8.0. The effluent at this point looked clear and free of protein as measured spectrophotometrically at A280. Crystalline fructose greens feed was prepared by diluting crystalline fructose greens down to 60% DS with RO water, followed by adjusting the pH to 8.0 and then addition of 28 ppm MnCl$_2$ and 10 mM Tris buffer pH 8.0.

Feed was then pumped through the 30 ml fixed bed reactors at a rate of 8 bed volumes per hour (BV/h) with the jacketed columns heated with a recirculating water bath to a temperature of 57° C. The reactor effluent was collected and analysed by FT-IR to provide a relative concentration of allulose and fructose. This process was continued for a total of 5 days. The feed rate was adjusted from 8 bed volumes per hour down to 6 bed volumes per hour over the course of the test production run in order to maintain conversion rate.

2. Scale-Up 300 ml Fixed Bed Reactor

In order to test scaled-up efficiency of immobilisation, a larger fixed bed reactor was created in jacketed columns of approximately 300 ml volume (25 mm×600 mm column dimensions). Both XAD2 and A568 resin was washed several times with water to remove fines and any residuals from manufacturing. 10 g of lyophilised epimerase was dissolved in approximately 100 ml of water. Approximately 300 ml of A568 resin was packed into the 300 ml jacketed column and peristaltic pumps were used to recycle the epimerase solution through the fixed bed for approximately two hours at room temperature. The columns were then washed with 5 bed volumes of Tris buffer 100 mM, pH 8.0, at room temperature. The effluent at this point looked clear and free of protein as measured spectrophotometrically at A280. Crystalline fructose greens feed was prepared by diluting crystalline fructose greens down to 60% DS with RO water, followed by adjusting the pH to 8.0 and then addition of 28 ppm MnCl$_2$ and 10 mM Tris buffer pH 8.0. Feed was then pumped through the 30 ml fixed bed reactors at a rate of 8 bed volumes per hour (BV/h) with the jacketed columns heated with a recirculating water bath to a temperature of 57° C. The reactor effluent was collected and analysed by FT-IR to provide a relative concentration of allulose and fructose. This process was continued for a total of 4 days. The feed rate was adjusted from eight bed volumes per hour down to two bed volumes per hour over the course of the test production run. Additionally, the column was allowed to sit at room temperature for two weeks and then restarted to determine the epimerase stability during column storage.

Results and Discussion

Figure 13:
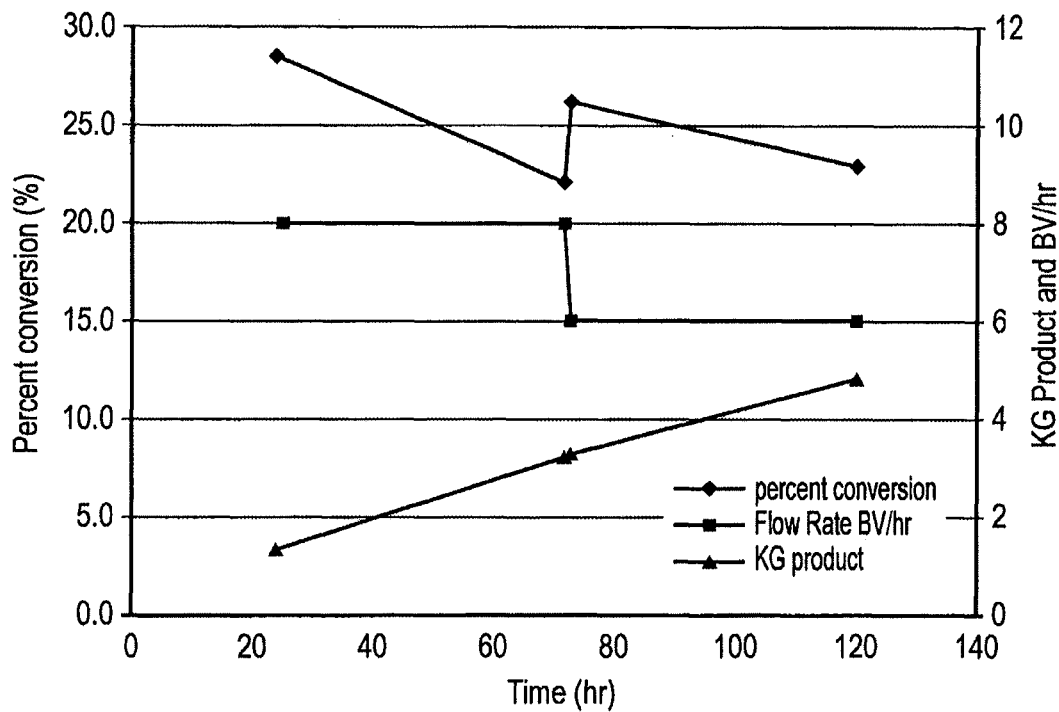
FIG. 13 is a graph showing the rate of allulose conversion by DS P3E in a 30 ml fixed bed reactor packed with A568 resin.

The 30 ml column with XAD2 displayed no significant conversion for any of the samples checked and, therefore, no further analysis was performed. However, significant conversion was observed with Dowex A568. FIG. 13 shows the time course of reaction for the 30 ml fixed bed reactor with A568 resin. More than 4 kg of allulose was produced over the course of 120 hour fixed bed conversion containing just 1 g of epimerase. The percentage conversion gradually decreased over the course of the 120 hours and the flow rate through the column was reduced at 72 hours to compensate. Near equilibrium concentrations of allulose were produced during the reaction.

Figure 14:
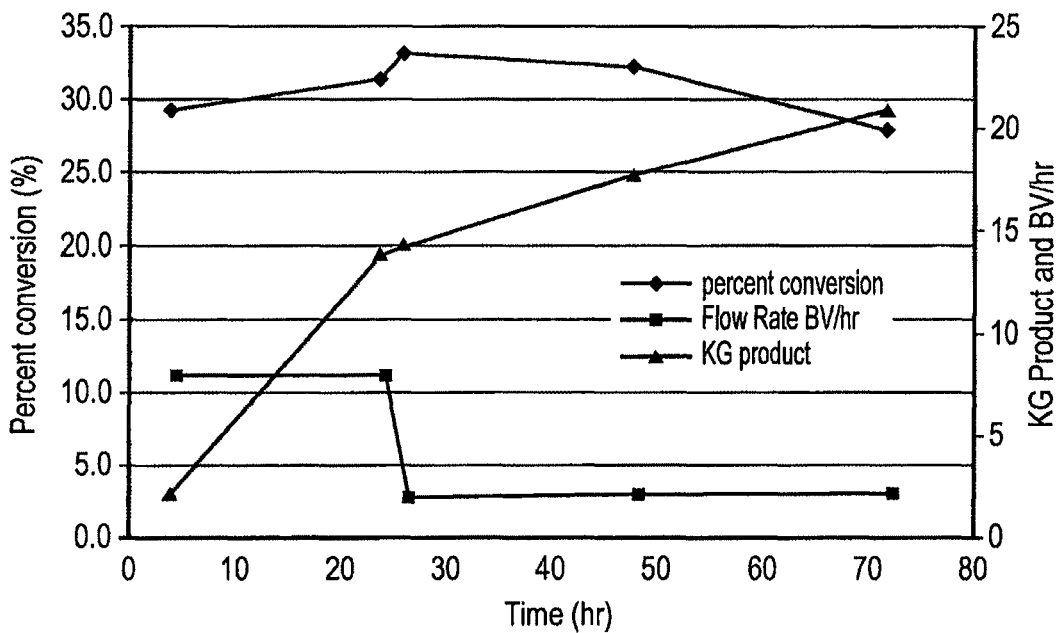
FIG. 14 is a graph showing the rate of allulose conversion by DS P3E in a 300 ml fixed bed reactor packed with A568 resin.

FIG. 14 displays the course of the 300 ml reaction with A568 resin. Flow rate was decreased at 24 hours due to limitations in the amount of feed available (86 l of feed were used in 72 hours). More than 20 kg of allulose was produced in 72 hours from 10 g of epimerase. The conversion rate was still high at the end of 72 hours, although some decline in performance was observed.

Epimerase stability in solution has previously been determined in flask reactions. More than 90% of activity is lost within 8 hours at 53° C. In this example, the conversion was carried out at 57° C. A higher temperature is advantageous in terms of reaction rate, equilibrium ratio, and microbiological stability. In this example, significant epimerase activity remained even after 120 hours.

In the large scale reaction, which was feed limited, 20 kg of allulose was produced using 10 g of epimerase, resulting in a net epimerase dosing rate of 0.05% (m/m). In the small scale reaction, 4.8 kg of allulose was produced from 1 g of epimerase, resulting in a net epimerase dosing rate of 0.02% (m/m). In standard fructose production, immobilised glucoisomerase is used at a rate of 0.01-0.005% (ml), although this is over the course of 6-12 months of operation.

The invention claimed is:

1. A method of manufacturing a product comprising the steps of:
   (a) producing allulose by contacting a protein having allulose 3-epimerase activity with a fructose substrate under conditions such that the fructose substrate is converted into allulose;
   wherein the allulose is at least partially purified; and
   wherein the protein having allulose 3-epimerase activity comprises an amino acid sequence having 90% to 99% sequence identity to the amino acid sequence of SEQ ID NO: 6; and
   (b) using the allulose produced in step (a) to manufacture the product.

2. The method of claim 1, wherein the product is a food product, a beverage product, a pharmaceutical product, a nutritional product, a sports product, or a cosmetic product.

3. The method of claim 2, wherein the food product is a confectionery product, a dessert product, a cereal product, a baked good, a frozen dairy product, a meat product, a dairy product, a condiment, a snack bar, a soup, a dressing, a mix, a prepared food, a baby food, a diet preparation, a syrup, a food coating or frosting, a dried fruit, a sauce, a gravy, or a jam or jelly.

4. The method of claim 2, wherein the beverage product is a carbonated beverage, a non-carbonated beverage, a fruit-flavoured beverage, a fruit juice, a tea, milk, or coffee.

5. The method of claim 1, wherein the protein having allulose 3-epimerase activity is present in an isolated host cell transformed with a vector comprising a nucleic acid molecule encoding the protein.

6. The method of claim 1, wherein the protein having allulose 3-epimerase activity is in isolated form.

7. The method of claim 1, wherein the conditions of step (a) comprise maintaining the protein and the fructose substrate at a temperature between 25° C. and 75° C.

8. The method of claim 1, wherein the conditions of step (a) comprise maintaining the protein and the fructose substrate between pH 4 and pH 10.

9. The method of claim 1, wherein the conditions of step (a) comprise maintaining the fructose substrate concentration between 75% and 95% (w/v).

10. The method of claim 1, wherein the protein having allulose 3-epimerase activity comprises an amino acid sequence having 90% to 95% sequence identity to the amino acid sequence of SEQ ID NO: 6.

11. A method of manufacturing a product comprising the steps of:
    (a) producing allulose by:
       (i) providing a vector comprising a nucleic acid molecule having a polynucleotide sequence encoding a protein having allulose 3-epimerase activity;
       (ii) synthesizing the protein having allulose 3-epimerase activity from the vector;
       (iii) contacting fructose with the protein having allulose 3-epimerase activity and maintaining the fructose and the protein under conditions to permit the conversion of fructose to allulose;
    wherein the protein having allulose 3-epimerase activity comprises an amino acid sequence having at least 90% sequence identity to the amino acid sequence of SEQ ID NO: 6; and
    (b) using the allulose produced in step (a) to manufacture the product.

12. The method of claim 11, wherein the product is a food product, a beverage product, a pharmaceutical product, a nutritional product, a sports product, or a cosmetic product.

13. The method of claim 12, wherein the food product is a confectionery product, a dessert product, a cereal product, a baked good, a frozen dairy product, a meat product, a dairy product, a condiment, a snack bar, a soup, a dressing, a mix, a prepared food, a baby food, a diet preparation, a syrup, a food coating or frosting, a dried fruit, a sauce, a gravy, or a jam or jelly.

14. The method of claim 12, wherein the beverage product is a carbonated beverage, a non-carbonated beverage, a fruit-flavoured beverage, a fruit juice, a tea, milk, or coffee.

15. The method of claim 11, wherein the allulose produced in step (a) is at least partially purified.

16. The method of claim 11, wherein the protein having allulose 3-epimerase activity encoded by the polynucleotide sequence is synthesized by transforming competent host cells with the vector and, optionally, culturing the transformed host cells.

17. The method of claim 11, wherein the step of synthesizing the protein having allulose 3-epimerase activity comprises synthesizing the protein by in vitro translation and subsequently isolating the protein.

18. The method of claim 16, wherein the step of contacting fructose with the protein having allulose 3-epimerase activity comprises mixing the transformed host cells with the fructose.

19. The method of claim 16, wherein the step of contacting fructose with the protein having allulose 3-epimerase activity comprises culturing the transformed host cells to produce the protein having allulose 3-epimerase activity, isolating the protein having allulose 3-epimerase activity from the host cells, and mixing the protein having allulose 3-epimerase activity with the fructose.

20. The method of claim 19, wherein the protein having allulose 3-epimerase activity is immobilized on a substrate after isolation of the protein.

21. The method of claim 11, wherein the protein having allulose 3-epimerase activity comprises an amino acid sequence having at least 95% sequence identity to the amino acid sequence of SEQ ID NO: 6.

22. The method of claim 11, wherein the protein having allulose 3-epimerase activity comprises an amino acid sequence having 90% to 99% sequence identity to the amino acid sequence of SEQ ID NO: 6.

23. The method of claim 11, wherein the protein having allulose 3-epimerase activity comprises an amino acid sequence having 90% to 95% sequence identity to the amino acid sequence of SEQ ID NO: 6.

* * * * *

SEQUENCE LISTING

<160> NUMBER OF SEQ ID NOS: 15

<210> SEQ ID NO 1
<211> LENGTH: 903
<212> TYPE: DNA
<213> ORGANISM: Clostridium scindens
<220> FEATURE:
<221> NAME/KEY: CDS
<222> LOCATION: (4)..(888)

<400> SEQUENCE: 1 cat atg aat cgt att ggc att ttt atg aat ttt tgg gtg aag aac tgg      48

```
        Met Asn Arg Ile Gly Ile Phe Met Asn Phe Trp Val Lys Asn Trp
        1               5                  10                  15 gac gct gac cac gtt aag tac atc aag aag gtg tcg ggc ctg ggc ttt        96
Asp Ala Asp His Val Lys Tyr Ile Lys Lys Val Ser Gly Leu Gly Phe
                    20                  25                  30 gat att ctg gaa ttt cag gca caa gct ctg ctg gaa atg gat aaa tct       144
Asp Ile Leu Glu Phe Gln Ala Gln Ala Leu Leu Glu Met Asp Lys Ser
            35                  40                  45 cgt atg gac gaa gtg cgc cag gcg gcc aag gat aac ggc att gaa ctg       192
Arg Met Asp Glu Val Arg Gln Ala Ala Lys Asp Asn Gly Ile Glu Leu
        50                  55                  60 acc tat tct ctg ggt ctg aat ccg aaa tac gat gtg gca agt ccg gac       240
Thr Tyr Ser Leu Gly Leu Asn Pro Lys Tyr Asp Val Ala Ser Pro Asp
    65                  70                  75 gct aag gtt cgt gaa ggc ggt atc gaa tat ctg aaa cgt att gtg gaa       288
Ala Lys Val Arg Glu Gly Gly Ile Glu Tyr Leu Lys Arg Ile Val Glu
80                  85                  90                  95 cgc atc ggc tac atg gaa ggc aag ctg ctg tca ggc gtt aac tat gcg       336
Arg Ile Gly Tyr Met Glu Gly Lys Leu Leu Ser Gly Val Asn Tyr Ala
                    100                 105                 110 ggc tgg ggt tcg ccg gat tac att gtc gat gac aaa agc gaa att gtg       384
Gly Trp Gly Ser Pro Asp Tyr Ile Val Asp Asp Lys Ser Glu Ile Val
                115                 120                 125 gaa cat agc atc gaa agc gtg cgt cag gtc atc aaa acc gcc gaa gat       432
Glu His Ser Ile Glu Ser Val Arg Gln Val Ile Lys Thr Ala Glu Asp
            130                 135                 140 tat gac gtg acg tac tgc gtt gaa gtg gtt aac cgc ttt gaa ggc att       480
Tyr Asp Val Thr Tyr Cys Val Glu Val Val Asn Arg Phe Glu Gly Ile
        145                 150                 155 gtt atg aat acc gcg aaa gaa gcc att gaa tat gtc aaa caa atc gat       528
Val Met Asn Thr Ala Lys Glu Ala Ile Glu Tyr Val Lys Gln Ile Asp
160                 165                 170                 175 agc gac aag att ggt atc ctg ctg gat acg tac cac atg aac atc gaa       576
Ser Asp Lys Ile Gly Ile Leu Leu Asp Thr Tyr His Met Asn Ile Glu
                    180                 185                 190 gaa ggc agt att ggt gat gcg atc cgt tcc gtt ggc ggt tat ctg aaa       624
Glu Gly Ser Ile Gly Asp Ala Ile Arg Ser Val Gly Gly Tyr Leu Lys
                195                 200                 205 aat ttc cac acg ggc gaa aac aat cgc gtc gtg ccg ggc aag ggt cat       672
Asn Phe His Thr Gly Glu Asn Asn Arg Val Val Pro Gly Lys Gly His
            210                 215                 220 ctg gat tgg gac gaa att ttt ggc gca ctg cac gat att gac tac cag       720
Leu Asp Trp Asp Glu Ile Phe Gly Ala Leu His Asp Ile Asp Tyr Gln
        225                 230                 235 ggt cgc atc gtc tcc gaa ccg ttc gtg caa atg ggc ggt gaa gtg gct       768
Gly Arg Ile Val Ser Glu Pro Phe Val Gln Met Gly Gly Glu Val Ala
240                 245                 250                 255 cgt gat atc aaa gtt tgg cgc gat ctg gtc gaa gac ccg agc gaa gaa       816
Arg Asp Ile Lys Val Trp Arg Asp Leu Val Glu Asp Pro Ser Glu Glu
                    260                 265                 270 gtt ctg gat gaa gaa gcg cgt ttt ctg ctg aat ttc gaa aaa gac atg       864
Val Leu Asp Glu Glu Ala Arg Phe Leu Leu Asn Phe Glu Lys Asp Met
                275                 280                 285 att cgc aag cac tat ggt atc gcc taaagatctg gatcc                      903
Ile Arg Lys His Tyr Gly Ile Ala
            290                 295

<210> SEQ ID NO 2
<211> LENGTH: 295
<212> TYPE: PRT
```

<213> ORGANISM: Clostridium scindens

<400> SEQUENCE: 2

Met Asn Arg Ile Gly Ile Phe Met Asn Phe Trp Val Lys Asn Trp Asp
1               5                   10                  15

Ala Asp His Val Lys Tyr Ile Lys Lys Val Ser Gly Leu Gly Phe Asp
            20                  25                  30

Ile Leu Glu Phe Gln Ala Gln Ala Leu Leu Glu Met Asp Lys Ser Arg
        35                  40                  45

Met Asp Glu Val Arg Gln Ala Ala Lys Asp Asn Gly Ile Glu Leu Thr
50                  55                  60

Tyr Ser Leu Gly Leu Asn Pro Lys Tyr Asp Val Ala Ser Pro Asp Ala
65                  70                  75                  80

Lys Val Arg Glu Gly Gly Ile Glu Tyr Leu Lys Arg Ile Val Glu Arg
                85                  90                  95

Ile Gly Tyr Met Glu Gly Lys Leu Leu Ser Gly Val Asn Tyr Ala Gly
            100                 105                 110

Trp Gly Ser Pro Asp Tyr Ile Val Asp Lys Ser Glu Ile Val Glu
        115                 120                 125

His Ser Ile Glu Ser Val Arg Gln Val Ile Lys Thr Ala Glu Asp Tyr
130                 135                 140

Asp Val Thr Tyr Cys Val Glu Val Val Asn Arg Phe Glu Gly Ile Val
145                 150                 155                 160

Met Asn Thr Ala Lys Glu Ala Ile Glu Tyr Val Lys Gln Ile Asp Ser
                165                 170                 175

Asp Lys Ile Gly Ile Leu Leu Asp Thr Tyr His Met Asn Ile Glu Glu
            180                 185                 190

Gly Ser Ile Gly Asp Ala Ile Arg Ser Val Gly Gly Tyr Leu Lys Asn
        195                 200                 205

Phe His Thr Gly Glu Asn Asn Arg Val Val Pro Gly Lys Gly His Leu
210                 215                 220

Asp Trp Asp Glu Ile Phe Gly Ala Leu His Asp Ile Asp Tyr Gln Gly
225                 230                 235                 240

Arg Ile Val Ser Glu Pro Phe Val Gln Met Gly Gly Glu Val Ala Arg
                245                 250                 255

Asp Ile Lys Val Trp Arg Asp Leu Val Glu Asp Pro Ser Glu Glu Val
            260                 265                 270

Leu Asp Glu Glu Ala Arg Phe Leu Leu Asn Phe Glu Lys Asp Met Ile
        275                 280                 285

Arg Lys His Tyr Gly Ile Ala
290                 295

<210> SEQ ID NO 3
<211> LENGTH: 885
<212> TYPE: DNA
<213> ORGANISM: Clostridium hylemonae
<220> FEATURE:
<221> NAME/KEY: CDS
<222> LOCATION: (4)..(870)

<400> SEQUENCE: 3

```
cat atg aaa cac ggt atc tat tac gcc tat tgg gaa caa gaa tgg gca      48
    Met Lys His Gly Ile Tyr Tyr Ala Tyr Trp Glu Gln Glu Trp Ala
    1               5                   10                  15 gca gac tac aaa cgc tat gtg gaa aaa gtg gca aaa ctg ggc ttc gat      96
Ala Asp Tyr Lys Arg Tyr Val Glu Lys Val Ala Lys Leu Gly Phe Asp
            20                  25                  30
```

```
att ctg gaa atc ggc gcc ggt ccg ctg ccg gaa tat gca gaa cag gac      144
Ile Leu Glu Ile Gly Ala Gly Pro Leu Pro Glu Tyr Ala Glu Gln Asp
            35                  40                  45 gtt aaa gaa ctg aaa aag tgc gct caa gat aac ggc att acc ctg acg      192
Val Lys Glu Leu Lys Lys Cys Ala Gln Asp Asn Gly Ile Thr Leu Thr
        50                  55                  60 gcg ggc tac ggt ccg acc ttt aac cat aat atc ggc agc tct gat gct      240
Ala Gly Tyr Gly Pro Thr Phe Asn His Asn Ile Gly Ser Ser Asp Ala
    65                  70                  75 ggt gtg cgt gaa gaa gcg ctg gaa tgg tat aaa cgc ctg ttc gaa gtt      288
Gly Val Arg Glu Glu Ala Leu Glu Trp Tyr Lys Arg Leu Phe Glu Val
80                  85                  90                  95 ctg gcc gaa ctg gac att cac ctg atc ggc ggt gca ctg tat agt tac      336
Leu Ala Glu Leu Asp Ile His Leu Ile Gly Gly Ala Leu Tyr Ser Tyr
                100                 105                 110 tgg ccg gtc gat ttt gct aac gcg gac aaa acg gaa gat tgg aag tgg      384
Trp Pro Val Asp Phe Ala Asn Ala Asp Lys Thr Glu Asp Trp Lys Trp
            115                 120                 125 tcc gtg gag ggt atg cag cgt ctg gcc ccg gcg gcg gca aaa tac gat      432
Ser Val Glu Gly Met Gln Arg Leu Ala Pro Ala Ala Ala Lys Tyr Asp
        130                 135                 140 att aac ctg ggt atg gaa gtt ctg aat cgc ttt gaa tca cat atc ctg      480
Ile Asn Leu Gly Met Glu Val Leu Asn Arg Phe Glu Ser His Ile Leu
    145                 150                 155 aat acc gcc gaa gaa ggc gtc aaa ttc gtg gaa gaa gtt ggt atg gac      528
Asn Thr Ala Glu Glu Gly Val Lys Phe Val Glu Glu Val Gly Met Asp
160                 165                 170                 175 aac gtg aag gtt atg ctg gat acg ttc cac atg aat att gaa gaa caa      576
Asn Val Lys Val Met Leu Asp Thr Phe His Met Asn Ile Glu Glu Gln
                180                 185                 190 tcg att ggc ggt gcc atc cgt cgc gca ggc aaa ctg ctg ggt cat ttt      624
Ser Ile Gly Gly Ala Ile Arg Arg Ala Gly Lys Leu Leu Gly His Phe
            195                 200                 205 cac acc ggc gaa tgt aat cgt atg gtg ccg ggc aag ggt cgt att ccg      672
His Thr Gly Glu Cys Asn Arg Met Val Pro Gly Lys Gly Arg Ile Pro
        210                 215                 220 tgg cgc gaa atc ggt gac gct ctg cgt gat atc ggc tac gac ggt acg      720
Trp Arg Glu Ile Gly Asp Ala Leu Arg Asp Ile Gly Tyr Asp Gly Thr
    225                 230                 235 gca gtc atg gaa ccg ttc gtg cgt atg ggt ggt cag gtt ggt gca gat      768
Ala Val Met Glu Pro Phe Val Arg Met Gly Gly Gln Val Gly Ala Asp
240                 245                 250                 255 att aaa gtc tgg cgt gac atc tct cgc ggt gcc gat gaa gca cag ctg      816
Ile Lys Val Trp Arg Asp Ile Ser Arg Gly Ala Asp Glu Ala Gln Leu
                260                 265                 270 gat gac gat gct cgt cgc gcg ctg gaa ttt caa cgc tat atg ctg gaa      864
Asp Asp Asp Ala Arg Arg Ala Leu Glu Phe Gln Arg Tyr Met Leu Glu
            275                 280                 285 tgg aag taaagatctg gatcc                                              885
Trp Lys
```

<210> SEQ ID NO 4
<211> LENGTH: 289
<212> TYPE: PRT
<213> ORGANISM: Clostridium hylemonae

<400> SEQUENCE: 4

```
Met Lys His Gly Ile Tyr Tyr Ala Tyr Trp Glu Gln Glu Trp Ala Ala
1               5                   10                  15
```

```
Asp Tyr Lys Arg Tyr Val Glu Lys Val Ala Lys Leu Gly Phe Asp Ile
            20                  25                  30

Leu Glu Ile Gly Ala Gly Pro Leu Pro Glu Tyr Ala Glu Gln Asp Val
        35                  40                  45

Lys Glu Leu Lys Lys Cys Ala Gln Asp Asn Gly Ile Thr Leu Thr Ala
 50                  55                  60

Gly Tyr Gly Pro Thr Phe Asn His Asn Ile Gly Ser Ser Asp Ala Gly
 65                  70                  75                  80

Val Arg Glu Glu Ala Leu Glu Trp Tyr Lys Arg Leu Phe Glu Val Leu
                85                  90                  95

Ala Glu Leu Asp Ile His Leu Ile Gly Gly Ala Leu Tyr Ser Tyr Trp
            100                 105                 110

Pro Val Asp Phe Ala Asn Ala Asp Lys Thr Glu Asp Trp Lys Trp Ser
        115                 120                 125

Val Glu Gly Met Gln Arg Leu Ala Pro Ala Ala Lys Tyr Asp Ile
    130                 135                 140

Asn Leu Gly Met Glu Val Leu Asn Arg Phe Glu Ser His Ile Leu Asn
145                 150                 155                 160

Thr Ala Glu Glu Gly Val Lys Phe Val Glu Glu Val Gly Met Asp Asn
                165                 170                 175

Val Lys Val Met Leu Asp Thr Phe His Met Asn Ile Glu Glu Gln Ser
            180                 185                 190

Ile Gly Gly Ala Ile Arg Arg Ala Gly Lys Leu Leu Gly His Phe His
        195                 200                 205

Thr Gly Glu Cys Asn Arg Met Val Pro Gly Lys Gly Arg Ile Pro Trp
210                 215                 220

Arg Glu Ile Gly Asp Ala Leu Arg Asp Ile Gly Tyr Asp Gly Thr Ala
225                 230                 235                 240

Val Met Glu Pro Phe Val Arg Met Gly Gly Gln Val Gly Ala Asp Ile
                245                 250                 255

Lys Val Trp Arg Asp Ile Ser Arg Gly Ala Asp Glu Ala Gln Leu Asp
            260                 265                 270

Asp Asp Ala Arg Arg Ala Leu Glu Phe Gln Arg Tyr Met Leu Glu Trp
        275                 280                 285

Lys
```

<210> SEQ ID NO 5
<211> LENGTH: 885
<212> TYPE: DNA
<213> ORGANISM: Desmospora sp.8437
<220> FEATURE:
<221> NAME/KEY: CDS
<222> LOCATION: (4)..(870)

<400> SEQUENCE: 5

```
cat atg aaa tac ggt gtc tac ttt gct tac tgg gaa gat tcg tgg gat      48
    Met Lys Tyr Gly Val Tyr Phe Ala Tyr Trp Glu Asp Ser Trp Asp
     1               5                  10                  15 gtt gac ttt gaa aaa tac gtt cgc aag gtg aaa aaa ctg ggc ttt gat      96
Val Asp Phe Glu Lys Tyr Val Arg Lys Val Lys Lys Leu Gly Phe Asp
                20                  25                  30 att ctg gaa gtt gca gca ctg ggt ctg gtc aac ctg ccg gaa gaa aaa     144
Ile Leu Glu Val Ala Ala Leu Gly Leu Val Asn Leu Pro Glu Glu Lys
            35                  40                  45 ctg gaa cgt ctg aag cag ctg gcg gaa caa cat gac att atc ctg acc     192
Leu Glu Arg Leu Lys Gln Leu Ala Glu Gln His Asp Ile Ile Leu Thr
        50                  55                  60
```

| | | |
|---|---|---|
| gcc ggc att ggt ctg ccg aaa gaa tat gat gtc agc tct acg gac aaa<br>Ala Gly Ile Gly Leu Pro Lys Glu Tyr Asp Val Ser Ser Thr Asp Lys<br>65                    70                       75 | | 240 |
| aaa gtg cgt cgc aat ggc atc tcc ttt atg aaa aag gtt atg gat gca<br>Lys Val Arg Arg Asn Gly Ile Ser Phe Met Lys Lys Val Met Asp Ala<br>80                        85                    90                     95 | | 288 |
| atg cat cag gct ggt att cac cgt att ggc ggc acc gtg tat agc tac<br>Met His Gln Ala Gly Ile His Arg Ile Gly Gly Thr Val Tyr Ser Tyr<br>                  100                          105                       110 | | 336 |
| tgg ccg gtt gat tac agt tgc tcc ttc gac aaa ccg gcg gtt cgc aag<br>Trp Pro Val Asp Tyr Ser Cys Ser Phe Asp Lys Pro Ala Val Arg Lys<br>                  115                         120                      125 | | 384 |
| cac tca att gaa tcg gtc cgt gaa ctg gcg gaa tat gcc cgc cag tac<br>His Ser Ile Glu Ser Val Arg Glu Leu Ala Glu Tyr Ala Arg Gln Tyr<br>                  130                       135                      140 | | 432 |
| aac att acc ctg ctg atc gaa acg ctg aac cgc ttt gaa caa ttc ctg<br>Asn Ile Thr Leu Leu Ile Glu Thr Leu Asn Arg Phe Glu Gln Phe Leu<br>145                    150                     155 | | 480 |
| ctg aat gat gcc gaa gaa gcg gtt gcc tat gtc aaa gaa gtg gat gaa<br>Leu Asn Asp Ala Glu Glu Ala Val Ala Tyr Val Lys Glu Val Asp Glu<br>160                      165                    170                  175 | | 528 |
| ccg aac gtc aag gtg atg ctg gac acc ttc cac atg aac atc gaa gaa<br>Pro Asn Val Lys Val Met Leu Asp Thr Phe His Met Asn Ile Glu Glu<br>                  180                       185                    190 | | 576 |
| gat cac atc gca gac gct atc cgt tac acg ggc gat cat ctg ggt cag<br>Asp His Ile Ala Asp Ala Ile Arg Tyr Thr Gly Asp His Leu Gly Gln<br>                  195                       200                    205 | | 624 |
| ctg cac atc ggc gaa gcc aac cgc aaa gtg ccg ggc aag ggt agt atg<br>Leu His Ile Gly Glu Ala Asn Arg Lys Val Pro Gly Lys Gly Ser Met<br>210                    215                    220 | | 672 |
| ccg tgg acc gaa att ggc caa gca ctg aaa gat atc cgt tat gac ggt<br>Pro Trp Thr Glu Ile Gly Gln Ala Leu Lys Asp Ile Arg Tyr Asp Gly<br>225                    230                     235 | | 720 |
| tac gtg gtt atg gaa ccg ttc att aaa acc ggc ggt cag gtt ggc cgt<br>Tyr Val Val Met Glu Pro Phe Ile Lys Thr Gly Gly Gln Val Gly Arg<br>240                    245                    250                  255 | | 768 |
| gat atc aaa ctg tgg cgc gac ctg agc ggt aat gca acg gaa gaa caa<br>Asp Ile Lys Leu Trp Arg Asp Leu Ser Gly Asn Ala Thr Glu Glu Gln<br>                  260                       265                    270 | | 816 |
| ctg gat cgc gaa ctg gct gaa tct ctg gaa ttt gtg aaa gca gct ttc<br>Leu Asp Arg Glu Leu Ala Glu Ser Leu Glu Phe Val Lys Ala Ala Phe<br>275                    280                    285 | | 864 |
| ggt gaa taaagatctg gatcc<br>Gly Glu | | 885 |

<210> SEQ ID NO 6
<211> LENGTH: 289
<212> TYPE: PRT
<213> ORGANISM: Desmospora sp.8437

<400> SEQUENCE: 6

Met Lys Tyr Gly Val Tyr Phe Ala Tyr Trp Glu Asp Ser Trp Asp Val
1                   5                   10                   15

Asp Phe Glu Lys Tyr Val Arg Lys Val Lys Lys Leu Gly Phe Asp Ile
                  20                       25                   30

Leu Glu Val Ala Ala Leu Gly Leu Val Asn Leu Pro Glu Glu Lys Leu
              35                       40                   45

Glu Arg Leu Lys Gln Leu Ala Glu Gln His Asp Ile Ile Leu Thr Ala
50                    55                     60

```
Gly Ile Gly Leu Pro Lys Glu Tyr Asp Val Ser Ser Thr Asp Lys Lys
 65                  70                  75                  80

Val Arg Arg Asn Gly Ile Ser Phe Met Lys Lys Val Met Asp Ala Met
                 85                  90                  95

His Gln Ala Gly Ile His Arg Ile Gly Gly Thr Val Tyr Ser Tyr Trp
            100                 105                 110

Pro Val Asp Tyr Ser Cys Ser Phe Asp Lys Pro Ala Val Arg Lys His
        115                 120                 125

Ser Ile Glu Ser Val Arg Glu Leu Ala Glu Tyr Ala Arg Gln Tyr Asn
    130                 135                 140

Ile Thr Leu Leu Ile Glu Thr Leu Asn Arg Phe Glu Gln Phe Leu Leu
145                 150                 155                 160

Asn Asp Ala Glu Glu Ala Val Ala Tyr Val Lys Glu Val Asp Glu Pro
                165                 170                 175

Asn Val Lys Val Met Leu Asp Thr Phe His Met Asn Ile Glu Glu Asp
            180                 185                 190

His Ile Ala Asp Ala Ile Arg Tyr Thr Gly Asp His Leu Gly Gln Leu
        195                 200                 205

His Ile Gly Glu Ala Asn Arg Lys Val Pro Gly Lys Gly Ser Met Pro
    210                 215                 220

Trp Thr Glu Ile Gly Gln Ala Leu Lys Asp Ile Arg Tyr Asp Gly Tyr
225                 230                 235                 240

Val Val Met Glu Pro Phe Ile Lys Thr Gly Gly Gln Val Gly Arg Asp
                245                 250                 255

Ile Lys Leu Trp Arg Asp Leu Ser Gly Asn Ala Thr Glu Glu Gln Leu
            260                 265                 270

Asp Arg Glu Leu Ala Glu Ser Leu Glu Phe Val Lys Ala Ala Phe Gly
        275                 280                 285

Glu
```

```
<210> SEQ ID NO 7
<211> LENGTH: 897
<212> TYPE: DNA
<213> ORGANISM: Clostridium cellulolyticum
<220> FEATURE:
<221> NAME/KEY: CDS
<222> LOCATION: (4)..(882)

<400> SEQUENCE: 7 cat atg aag cac ggc atc tat tac gcc tat tgg gaa caa gaa tgg gaa       48
    Met Lys His Gly Ile Tyr Tyr Ala Tyr Trp Glu Gln Glu Trp Glu
    1               5                  10                  15 gca gac tac aag tat tac atc gaa aag gtt gcg aag ctg ggt ttt gat       96
Ala Asp Tyr Lys Tyr Tyr Ile Glu Lys Val Ala Lys Leu Gly Phe Asp
                20                  25                  30 att ctg gaa atc gcg gcc tca ccg ctg ccg ttt tat tcg gac att cag      144
Ile Leu Glu Ile Ala Ala Ser Pro Leu Pro Phe Tyr Ser Asp Ile Gln
            35                  40                  45 atc aat gaa ctg aaa gcg tgc gcg cat ggc aac ggt att acc ctg acg      192
Ile Asn Glu Leu Lys Ala Cys Ala His Gly Asn Gly Ile Thr Leu Thr
        50                  55                  60 gtg ggc cac ggt ccg agc gcg gaa caa aat ctg agc agc ccg gac ccg      240
Val Gly His Gly Pro Ser Ala Glu Gln Asn Leu Ser Ser Pro Asp Pro
    65                  70                  75 gac atc cgt aaa aac gca aag gct ttc tat acc gat ctg ctg aaa cgc      288
Asp Ile Arg Lys Asn Ala Lys Ala Phe Tyr Thr Asp Leu Leu Lys Arg
80                  85                  90                  95
```

```
ctg tac aag ctg gac gtt cat ctg att ggc ggt gcc ctg tat tct tac      336
Leu Tyr Lys Leu Asp Val His Leu Ile Gly Gly Ala Leu Tyr Ser Tyr
                100                 105                 110 tgg ccg atc gat tac acc aag acg atc gat aag aag ggc gac tgg gaa      384
Trp Pro Ile Asp Tyr Thr Lys Thr Ile Asp Lys Lys Gly Asp Trp Glu
            115                 120                 125 cgt agt gtt gaa tcc gtc cgc gaa gtg gcc aag gtt gcg gaa gcc tgc      432
Arg Ser Val Glu Ser Val Arg Glu Val Ala Lys Val Ala Glu Ala Cys
        130                 135                 140 ggt gtc gat ttt tgt ctg gaa gtg ctg aac cgt ttc gaa aat tac ctg      480
Gly Val Asp Phe Cys Leu Glu Val Leu Asn Arg Phe Glu Asn Tyr Leu
    145                 150                 155 att aac acc gca cag gaa ggc gtc gat ttt gtg aaa caa gtt gac cat      528
Ile Asn Thr Ala Gln Glu Gly Val Asp Phe Val Lys Gln Val Asp His
160                 165                 170                 175 aac aat gtc aag gtg atg ctg gat acg ttc cac atg aat atc gaa gaa      576
Asn Asn Val Lys Val Met Leu Asp Thr Phe His Met Asn Ile Glu Glu
                180                 185                 190 gac agt att ggc ggt gcg atc cgt acc gcc ggc tcc tat ctg ggt cat      624
Asp Ser Ile Gly Gly Ala Ile Arg Thr Ala Gly Ser Tyr Leu Gly His
            195                 200                 205 ctg cac acg ggc gaa tgc aat cgc aaa gtt ccg ggc cgt ggt cgc att      672
Leu His Thr Gly Glu Cys Asn Arg Lys Val Pro Gly Arg Gly Arg Ile
        210                 215                 220 ccg tgg gtc gaa atc ggt gaa gca ctg gct gat att ggc tac aac ggt      720
Pro Trp Val Glu Ile Gly Glu Ala Leu Ala Asp Ile Gly Tyr Asn Gly
    225                 230                 235 tca gtg gtt atg gaa ccg ttt gtt cgt atg ggc ggc acc gtc ggc agc      768
Ser Val Val Met Glu Pro Phe Val Arg Met Gly Gly Thr Val Gly Ser
240                 245                 250                 255 aat att aaa gtg tgg cgc gat atc tct aac ggt gca gat gaa aag atg      816
Asn Ile Lys Val Trp Arg Asp Ile Ser Asn Gly Ala Asp Glu Lys Met
                260                 265                 270 ctg gac cgt gaa gct cag gca gct ctg gac ttc tca cgc tac gtg ctg      864
Leu Asp Arg Glu Ala Gln Ala Ala Leu Asp Phe Ser Arg Tyr Val Leu
            275                 280                 285 gaa tgt cat aaa cac tcg taaagatctg gatcc                             897
Glu Cys His Lys His Ser
        290

<210> SEQ ID NO 8
<211> LENGTH: 293
<212> TYPE: PRT
<213> ORGANISM: Clostridium cellulolyticum

<400> SEQUENCE: 8

Met Lys His Gly Ile Tyr Tyr Ala Tyr Trp Glu Gln Glu Trp Glu Ala
1               5                   10                  15

Asp Tyr Lys Tyr Tyr Ile Glu Lys Val Ala Lys Leu Gly Phe Asp Ile
            20                  25                  30

Leu Glu Ile Ala Ala Ser Pro Leu Pro Phe Tyr Ser Asp Ile Gln Ile
        35                  40                  45

Asn Glu Leu Lys Ala Cys Ala His Gly Asn Gly Ile Thr Leu Thr Val
    50                  55                  60

Gly His Gly Pro Ser Ala Glu Gln Asn Leu Ser Ser Pro Asp Pro Asp
65                  70                  75                  80

Ile Arg Lys Asn Ala Lys Ala Phe Tyr Thr Asp Leu Leu Lys Arg Leu
                85                  90                  95
```

```
Tyr Lys Leu Asp Val His Leu Ile Gly Gly Ala Leu Tyr Ser Tyr Trp
                100                 105                 110

Pro Ile Asp Tyr Thr Lys Thr Ile Asp Lys Lys Gly Asp Trp Glu Arg
            115                 120                 125

Ser Val Glu Ser Val Arg Glu Val Ala Lys Val Ala Glu Ala Cys Gly
        130                 135                 140

Val Asp Phe Cys Leu Glu Val Leu Asn Arg Phe Glu Asn Tyr Leu Ile
145                 150                 155                 160

Asn Thr Ala Gln Glu Gly Val Asp Phe Val Lys Gln Val Asp His Asn
                165                 170                 175

Asn Val Lys Val Met Leu Asp Thr Phe His Met Asn Ile Glu Glu Asp
            180                 185                 190

Ser Ile Gly Gly Ala Ile Arg Thr Ala Gly Ser Tyr Leu Gly His Leu
        195                 200                 205

His Thr Gly Glu Cys Asn Arg Lys Val Pro Gly Arg Gly Arg Ile Pro
    210                 215                 220

Trp Val Glu Ile Gly Ala Leu Ala Asp Ile Gly Tyr Asn Gly Ser
225                 230                 235                 240

Val Val Met Glu Pro Phe Val Arg Met Gly Gly Thr Val Gly Ser Asn
                245                 250                 255

Ile Lys Val Trp Arg Asp Ile Ser Asn Gly Ala Asp Glu Lys Met Leu
            260                 265                 270

Asp Arg Glu Ala Gln Ala Ala Leu Asp Phe Ser Arg Tyr Val Leu Glu
        275                 280                 285

Cys His Lys His Ser
    290

<210> SEQ ID NO 9
<211> LENGTH: 885
<212> TYPE: DNA
<213> ORGANISM: Clostridium scindens

<400> SEQUENCE: 9
aacagaatag gaatatttat gaatttctgg gttaagaact gggatgcaga tcatgtcaag      60
tatattaaaa aggtatccgg ccttggattt gatattctgg aattccaggc ccaggcgctt    120
ctggagatgg ataagagcag gatggatgag gtcaggcagg cggcaaagga caatggaatc    180
gaactgacct acagccttgg gctgaatcct aagtacgatg tcgcaagccc ggatgcaaaa    240
gtcagggaag gcggaatcga atatctgaag cggatcgtgg agcggattgg atacatggaa    300
ggaaaactgc tttccggagt caactatgcc ggctggggaa gcccggacta tcgtggat     360 gacaaaagcg agatcgtgga gcacagcatc gaaagcgtcc gccaggtcat taagacggca    420
gaagattatg acgtgactta ctgcgtggag gtcgtgaacc ggtttgaggg catcgtgatg    480
aatacggcaa aggaagccat cgagtacgtg aagcagattg acagtgataa gatcggaatc    540
ctgctggata cctatcatat gaacatcgag gaaggctcta taggagacgc catccgatct    600
gtaggcggat atctgaagaa cttccacact ggagagaaca accgggtcgt tccggggaag    660
gggcacctcg actgggatga aatatttgga gcgctccatg atatcgatta tcagggaagg    720
atcgtgtcag agccgttcgt ccagatgggc ggggaagtcg caagagacat caaggtatgg    780
agagatctgg tggaagatcc ttcagaagaa gtgctggatg aggaggcgcg cttccttctg    840 aatttttgaaa aggatatgat ccggaagcac tatggcatag cgtaa                    885

<210> SEQ ID NO 10
```

<211> LENGTH: 867
<212> TYPE: DNA
<213> ORGANISM: Clostridium hylemonae

<400> SEQUENCE: 10

```
aaacatggta tctattatgc atactgggaa caagaatggg cggccgacta caagcgctat    60
gttgaaaagg tggcaaagct tgggtttgac attctggaga tcggcgctgg gccgctgccg   120
gaatacgcag agcaggatgt gaaggaactg aagaaatgtg cgcaggacaa tgggatcacg   180
ctgacggccg atatggtcc gacgttcaac cacaatatcg gttcttcaga cgccggggta    240
agggaagagg cgctggaatg gtataagagg ttatttgaag tgctggcaga gcttgatatc   300
cacctgatcg gaggggcgct ctattcttac tggcctgtcg attttgcaaa cgccgataaa   360
acggaagact ggaagtggag tgtagagggc atgcagaggc tggcgccggc cgcggccaaa   420
tatgacatca acctgggcat ggaagttctg aaccggtttg agagccatat cctgaataca   480
gccgaggaag tgtgaagtt tgtagaggaa gtcggcatgg acaacgtaaa ggtcatgctg   540
gatacattcc atatgaatat agaagagcaa agcataggcg gcgcgatccg ccgggcagga   600
aaactgctcg ggcatttcca caccggagaa tgcaaccgca tggtgcccgg aagggacgt    660
attccatggc gtgagatagg ggatgctctc cgtgatatcg gatatgacgg aactgctgta   720
atggagccgt tcgttcgcat gggaggacag gtcggcgctg atatcaaggt gtggagagac   780
ataagccgtg agcagacga ggcacagctt gacgatgacg cgcgccgtgc gctggagttc    840
cagagatata tgctggagtg gaagtaa                                        867
```

<210> SEQ ID NO 11
<211> LENGTH: 867
<212> TYPE: DNA
<213> ORGANISM: Desmospora sp

<400> SEQUENCE: 11

```
aaatacggtg tctatttcgc ttactgggaa gactcgtggg atgtggattt cgagaagtac    60
gtgcggaaag tgaaaaagtt gggcttcgac atcctcgaag tggcggcatt gggtctcgtc   120
aaccttccgg aggagaaact ggagcggctg aaacaactcg ccgaacagca cgatatcatc   180
ctgacggccg ggatcggcct gccaaaggaa tacgatgtct cgtcaactga caaaaaggtg   240
cgccggaacg gcatctcctt catgaagaaa gtgatggacg cgatgcatca ggccggcatc   300
caccggatcg gcggcacggt ctactcgtat tggccggttg actacagttg ctccttcgac   360
aagccggccg taaggaagca cagcatcgaa agcgtcagag agctggcgga gtacgcacgg   420
cagtacaaca tcacactcct catcgaaacg ctcaaccggt ttgagcagtt tctcctgaac   480
gacgcggagg aagcagtcgc ctatgtgaag gaagtggacg agccgaatgt gaaagtcatg   540
ctcgacacat tccacatgaa catcgaggaa gaccacattg ccgatgccat ccgctacacc   600
ggtgaccacc tcggccaact gcacatcggc gaagcgaatc ggaaagtccc gggcaagggt   660
tcgatgcctt ggacagaaat cggacaggcg ctgaaagaca ttcgctacga tggctacgtt   720
gtcatggaac ccttcatcaa aaccggcgga caggtcggcc gggacatcaa gctctggcgc   780
gatctgtcgg gaaatgcgac ggaggaacag ttggaccggg agctggcaga gtcgctggaa   840
tttgtgaaag cggcgttcgg ggagtaa                                        867
```

<210> SEQ ID NO 12
<211> LENGTH: 879
<212> TYPE: DNA
<213> ORGANISM: Clostridium cellulolyticum

<400> SEQUENCE: 12

```
aaacatggta tatactacgc atattgggaa caagaatggg aagctgatta caaatactat    60
attgagaagg ttgcaaagct tggttttgat attctagaga ttgcagcttc accgctacct   120
ttttacagtg acattcagat taatgagctc aaggcatgtg cccatggcaa tggaattaca   180
cttacggtag gccatgggcc tagtgcagaa caaaacctgt cttctcccga ccccgatatt   240
cgcaaaaatg ctaaagcttt ttataccgat ttactcaaac gactttacaa gctggatgta   300
catttgatag gtggggcttt atattcttat tggccgatag attacacaaa gacaattgat   360
aaaaaaggcg attgggaacg cagcgttgaa agtgttcgag aagttgctaa ggtggccgaa   420
gcctgtggag tggatttctg cctagaggtt cttaatagat ttgagaatta tttaattaac   480
acagcacaag agggtgtaga ttttgtaaaa caggttgacc ataacaatgt aaaggtaatg   540
cttgatacct tccatatgaa tattgaggaa gatagtatcg gaggtgcaat caggactgcg   600
ggctcttact tgggacattt acacactggc gaatgtaatc gtaaagttcc cggcagagga   660
agaattccat gggtagaaat tggtgaggct cttgctgaca taggttataa cggtagtgtt   720
gttatggaac cttttgttag aatgggcgga actgtcggat ctaatattaa ggtttggcgt   780
gacattagta acggtgcaga tgagaaaatg ctggatagag aagcacaggc cgcacttgat   840
ttctccagat atgtattaga atgtcataaa cactcctga                          879
```

<210> SEQ ID NO 13
<211> LENGTH: 289
<212> TYPE: PRT
<213> ORGANISM: Artificial Sequence
<220> FEATURE:
<223> OTHER INFORMATION: Artificial variant of the ketose-3-epimerase of Desmospora sp. 8437.

<400> SEQUENCE: 13

```
Met Arg Tyr Gly Ile Tyr Tyr Ala Tyr Trp Glu Asp Ser Trp Asp Ala
1               5                   10                  15

Asp Phe Glu Lys Tyr Val Lys Val Lys Lys Leu Gly Phe Asp Ile
            20                  25                  30

Ile Glu Val Ala Ala Leu Gly Phe Val Asn Leu Pro Glu Glu Lys Leu
        35                  40                  45

Glu Thr Leu Arg Gln Leu Ala Glu Gln His Asp Ile Ile Leu Thr Ala
    50                  55                  60

Gly Tyr Gly Leu Pro Lys Glu Tyr Asn Val Ser Ser Pro Asp Lys Lys
65                  70                  75                  80

Val Arg Arg Asn Gly Ile Ser Phe Met Lys Lys Val Leu Asp Ala Met
                85                  90                  95

His Gln Leu Gly Ile His Arg Ile Gly Gly Thr Val Phe Ser Tyr Trp
            100                 105                 110

Pro Val Asp Tyr Ser Cys Ser Phe Asp Lys Pro Ala Val Arg Lys His
        115                 120                 125

Ala Ile Glu Ser Val Arg Glu Val Ala Glu Tyr Ala Arg Gln Tyr Asn
    130                 135                 140

Ile Thr Leu Ala Ile Glu Val Leu Asn Arg Phe Glu Gln Phe Val Leu
145                 150                 155                 160

Asn Asp Ala Glu Glu Ala Ile Ala Tyr Val Lys Glu Val Gly Glu Pro
                165                 170                 175

Asn Val Lys Val Met Leu Asp Thr Phe His Met Asn Ile Glu Glu Asp
            180                 185                 190
```

His Phe Ala Asp Ala Ile Arg Tyr Ala Gly Asp Leu Leu Gly Gln Leu
            195                 200                 205

His Ile Gly Glu Ala Asn Arg Lys Val Pro Gly Lys Gly Ser Leu Pro
        210                 215                 220

Trp Thr Glu Ile Gly Gln Ala Leu Lys Asp Ile Arg Tyr Asp Gly Tyr
225                 230                 235                 240

Val Ile Met Glu Pro Phe Val Lys Thr Gly Gly Thr Val Gly Arg Asp
                245                 250                 255

Val Lys Leu Trp Arg Asp Met Ser Gly Asn Ala Thr Glu Glu Gln Leu
            260                 265                 270

Asp Arg Glu Leu Ala Glu Ser Leu Glu Phe Val Arg Ala Ala Phe Gly
        275                 280                 285

Glu

<210> SEQ ID NO 14
<211> LENGTH: 289
<212> TYPE: PRT
<213> ORGANISM: Agrobacterium tumefaciens

<400> SEQUENCE: 14

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
            20                  25                  30

Ile Glu Val Ala Ala His His Ile Asn Glu Tyr Ser Asp Ala Glu Leu
        35                  40                  45

Ala Thr Ile Arg Lys Ser Ala Lys Asp Asn Gly Ile Ile Leu Thr Ala
    50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
        115                 120                 125

Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Ser Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

```
Asp Glu Asp Ala Arg Asn Ala Leu Ala Phe Ser Arg Phe Val Leu Gly
        275                 280                 285
Gly

<210> SEQ ID NO 15
<211> LENGTH: 290
<212> TYPE: PRT
<213> ORGANISM: Pseudomonas cichorii

<400> SEQUENCE: 15

Met Asn Lys Val Gly Met Phe Tyr Thr Tyr Trp Ser Thr Glu Trp Met
1               5                   10                  15

Val Asp Phe Pro Ala Thr Ala Lys Arg Ile Ala Gly Leu Gly Phe Asp
            20                  25                  30

Leu Met Glu Ile Ser Leu Gly Glu Phe His Asn Leu Ser Asp Ala Lys
        35                  40                  45

Lys Arg Glu Leu Lys Ala Val Ala Asp Leu Gly Leu Thr Val Met
    50                  55                  60

Cys Cys Ile Gly Leu Lys Ser Glu Tyr Asp Phe Ala Ser Pro Asp Lys
65                  70                  75                  80

Ser Val Arg Asp Ala Gly Thr Glu Tyr Val Lys Arg Leu Leu Asp Asp
            85                  90                  95

Cys His Leu Leu Gly Ala Pro Val Phe Ala Gly Leu Thr Phe Cys Ala
            100                 105                 110

Trp Pro Gln Ser Pro Leu Asp Met Lys Asp Lys Arg Pro Tyr Val
        115                 120                 125

Asp Arg Ala Ile Glu Ser Val Arg Arg Val Ile Lys Val Ala Glu Asp
            130                 135                 140

Tyr Gly Ile Ile Tyr Ala Leu Glu Val Val Asn Arg Phe Glu Gln Trp
145                 150                 155                 160

Leu Cys Asn Asp Ala Lys Glu Ala Ile Ala Phe Ala Asp Ala Val Asp
                165                 170                 175

Ser Pro Ala Cys Lys Val Gln Leu Asp Thr Phe His Met Asn Ile Glu
            180                 185                 190

Glu Thr Ser Phe Arg Asp Ala Ile Leu Ala Cys Lys Gly Lys Met Gly
        195                 200                 205

His Phe His Leu Gly Glu Ala Asn Arg Leu Pro Pro Gly Glu Gly Arg
    210                 215                 220

Leu Pro Trp Asp Glu Ile Phe Gly Ala Leu Lys Glu Ile Gly Tyr Asp
225                 230                 235                 240

Gly Thr Ile Val Met Glu Pro Phe Met Arg Lys Gly Gly Ser Val Ser
                245                 250                 255

Arg Ala Val Gly Val Trp Arg Asp Met Ser Asn Gly Ala Thr Asp Glu
            260                 265                 270

Glu Met Asp Glu Arg Ala Arg Ser Leu Gln Phe Val Arg Asp Lys
        275                 280                 285

Leu Ala
    290
```